(12) United States Patent
Obara et al.

(10) Patent No.: US 7,531,619 B2
(45) Date of Patent: May 12, 2009

(54) PROCESS FOR PRODUCING DENDRIMER, BUILDING BLOCK COMPOUND, AND PROCESS FOR PRODUCING THIOPHENE COMPOUND

(76) Inventors: Satoru Obara, c/o Photosensitive Materials Research Center, Toyo Gosei Co., Ltd., 2-1, Wakahagi 4-chome, Inbu-mura, Inba-gun (JP) 270-1609; Kentaro Tada, c/o Photosensitive Materials Research Center, Toyo Gosei Co., Ltd., 2-1, Wakahagi 4-chome, Inba-mura, Inba-gun (JP) 270-1609

( * ) Notice: Subject to any disclaimer, the term of this patent is extended or adjusted under 35 U.S.C. 154(b) by 563 days.

(21) Appl. No.: 10/521,689

(22) PCT Filed: Jul. 14, 2003

(86) PCT No.: PCT/JP03/08900

§ 371 (c)(1),
(2), (4) Date: Jul. 21, 2005

(87) PCT Pub. No.: WO2004/009669

PCT Pub. Date: Jan. 29, 2004

(65) Prior Publication Data

US 2006/0122364 A1    Jun. 8, 2006

(30) Foreign Application Priority Data

Jul. 18, 2002    (JP)    ............................. 2002-210221

(51) Int. Cl.
*C08G 75/06*    (2006.01)
*C08G 75/00*    (2006.01)
*C08G 61/00*    (2006.01)
*C08G 61/12*    (2006.01)

(52) U.S. Cl. ........................... 528/377; 528/378; 549/4; 549/59

(58) Field of Classification Search .................. 528/377, 528/378; 549/59, 4
See application file for complete search history.

(56) References Cited

U.S. PATENT DOCUMENTS 6,025,462 A    2/2000    Wang et al.

FOREIGN PATENT DOCUMENTS

| JP | 3074277 | 3/1997 |
|----|---------|--------|
| JP | 10-310561 | 11/1998 |
| JP | 2001-247861 | 9/2001 |
| JP | 2002-20740 | 1/2002 |

OTHER PUBLICATIONS

Grayson, S.M., et al, Convergent Dendrons and Dendrimers, From Synthesis to Applications, Chem. Rev. 101, pp. 3819-3867 (2001).

(Continued)

*Primary Examiner*—Duc Truong

(57) ABSTRACT

A method for producing a dendrimer having a structural repeating unit which is represented by formula (1) and which contains a linear portion including a thienylene moiety and a branch portion Y formed of an optionally substituted trivalent organic group. The method is based on the convergent method and includes reaction step 1 of converting α-position hydrogen of the thiophene ring of a thienylene-moiety-containing compound (a) for forming end moieties to an active group $V_1$ which undergoes Suzuki cross-coupling reaction, to thereby form compound (b); reaction step 2 of subjecting a compound (c) to Suzuki cross-coupling reaction with the compound (b), to thereby yield compound (d), the compound (c) having a linear portion and a branch portion Y and having, at the branch portion Y, two active groups $V_2$ which undergo Suzuki cross-coupling reaction with the active group $V_1$; reaction step 3 of converting α-position hydrogen of the thiophene ring of the thus-formed compound to an active group $V_1$ which undergoes Suzuki cross-coupling reaction, and reacting the compound (c) with the active group $V_1$, to thereby form a dendron of a subsequent generation; and a step of repeating the reaction step 3 in accordance with needs, to thereby form a dendrimer.

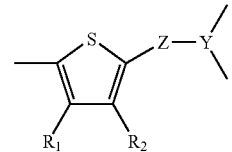

(1)

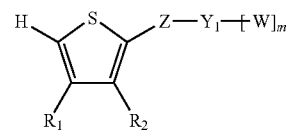

(a)

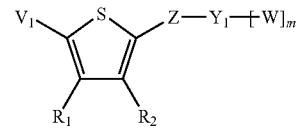

(b)

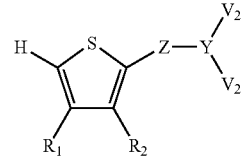

(c)

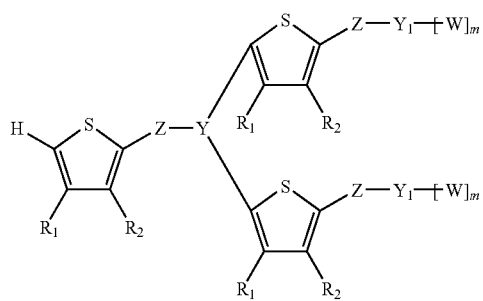

(d)

3 Claims, No Drawings

OTHER PUBLICATIONS

Malenfant, P., et al., Well-Defined Triblock Hybrid Dendrimers Based on Lengthy Oligothiophene Cores and Poly(benzyl ether) Dendrons, J. Am Chem. Soc., 120, 10990-10991 (1998).

Groenendaal, L., et al, Surface Functionalization of Polyether Dendrimers Using Palladium-Catalyzed Cross-Coupling Reactions, J. Org. Chem., 63, pp. 5675-5679 (1998).

Xia, C., et al, A First Synthesis of Thiophene Dendrimers, Organic Letters, vol. 4, No. 12, pp. 2067-2070 (2002).

Shirota, Y, et al., Starburst Molecules for Amorphous Molecular Materials, Chemistry Letters, pp. 1145-1148 (1989).

Miyaura, N., et al, Palladium-Catalyzed Cross-Coupling Reactions of Aryl and Vinylic Boron Compounds with Organic Halides, (J. of Synthetic Organic Chemistry, 46,p. 848 (1988).

Miyaura, N., et al, Palladium-Catalyzed Cross-Coupling Reactions of Organoboron Compounds, Chem. Rev., 95, 2457-2483 (1995).

Suzuki, A., Recent Advances in the Cross-Coupling Reactions of Organoboron Derivatives with Organic Electrophiles. Journal of Organometallic Chemistry, 576, pp. 147-168 (1999).

Kakimoto, M., Chemistry vol. 50, p. 608 (1995).

Kakimoto, M., Dendritic Macromolecules, Kobunshi (High Polymers, Japan) vol. 47, p. 804 (1998).

PROCESS FOR PRODUCING DENDRIMER, BUILDING BLOCK COMPOUND, AND PROCESS FOR PRODUCING THIOPHENE COMPOUND

TECHNICAL FIELD

The present invention relates to a method for producing a novel dendrimer having a thienylene moiety, which is a promising useful polymer material for producing a variety of high-function materials in the fields of chemistry, pharmaceuticals, electronic materials, etc. The invention also relates to a building block compound therefor and to a method for producing a thiophene compound.

BACKGROUND ART

Dendritic polymers, having a highly branched structure, are considered to exhibit physical and chemical properties and functions differing from those of conventional chain-form polymers. Dendritic polymers are generally classified into dendrimers and hyperbranched polymers. A dendrimer has a regularly controlled branching structure. Generally, a dendrimer has a radially and regularly branching structure in which polymer chains are branched from a core or a focal point serving as a center structure. The molecular weight of a dendrimer is virtually a single value; this is remarkably different from the case of conventional polymers, which exhibit a broad molecular weight distribution profile. Characteristic features of a dendrimer include low viscosity, high solubility, and amorphous nature, and these properties are of interest for various applications. In this connection, extensive studies have been carried out to impart new functions to the polymer through introduction of a variety of functional groups into end moieties serving as outer cores and a core serving as a center portion. In contrast, a hyperbranched polymer has structural regularity lower than that of a dendrimer and exhibits a wide distribution in terms of molecular weight and branching degree.

Among methods for synthesizing dendritic polymers, there have been known the "divergent method" in which branches are successively extended from a focal point or a core; the "convergent method" in which branching units for forming branch ends are successively connected and the thus-connected units are finally bonded to a focal point or a core; and self-condensation of a polyfunctional monomer of $AB_2$ type (A and B are mutually reactive functional groups). Among them, self-condensation of a polyfunctional monomer of $AB_2$ type is employed for synthesizing hyperbranched polymers exhibiting a molecular weight distribution, while the "divergent method" and "convergent method" are employed for synthesizing dendrimers having virtually a single molecular weight. The "divergent method" has some drawbacks. That is, the number of the outermost positions serving as reaction points increases as the generation number increases, thereby readily forming defects, and excessive amounts of reaction reagents are required so as to prevent defect formation. In contrast, the "convergent method" is advantageous. That is, the method is remarkably effective means for synthesizing, with high efficiency, a high-purity dendrimer having no defects, from the viewpoint of no requirement for excessive amounts of starting materials and easiness of purification of synthesis intermediates (see J. M. J. Frechet et al.; Chem. Rev. 101, 3819-3867 (2001)).

Examples of known repeating structures of the dendrimers synthesized through the aforementioned "convergent method" include polyaryl ether, polyaryl-alkylene, polyarylene, polyalkyl ether, polyarylalkene, polyamide, and polycarbonate. Specific examples include polybenzyl ether, polyphenylene, polyphenylene-vinylene, and polyphenylacetylene. Dendrimers will have a variety of functions in accordance with the combination of a core (center portion), end moieties (outer cores), and repeating structures for forming an inner skeleton. Thus, the repeating structure of dendrimers is a critical factor for determining characteristics of a functional material, and therefore, further new candidates of the structure and an effective synthesis method therefor are keenly demanded.

Meanwhile, thienylene moieties, having excellent electric properties and stability to heat and light, have been studied as base structures of conductive $\pi$-conjugated polymers and oligomers. In the field of dendritic polymers, there has been reported a dendrimer having an oligothiophene, structure serving as a core (center portion) and thienyl groups serving as end moieties (outer cores) (see J. M. J. Frechet et al.; J. Am. Chem. Soc., 120, 10990-10991 (1998) and J. Org. Chem., 63, 5675-5679 (1998)).

Among dendrimers having thienylene moieties in the repeating units (including synthesis methods therefor), a dendrimer having structural repeating units formed exclusively of a thenylene structure is disclosed (see Chuanjin Xla et al.; Organic Letters 2002, Vol. 4, No. 12, 2067-2070)).

The above synthesis method is a type of convergent method in which the generation of the dendrimer is increased through Grignard reaction or Stille coupling reaction. When Grignard reaction is employed, the reaction proceeds rapidly and exothermically, making temperature control in industrial production thereof difficult. In addition, in order to enhance yield of the synthesis, rigorous control of water content in the reaction system is essential. Thus, the Grignard-reaction-based method is unsuitable for large-scale production. When Stille coupling reaction is employed, a highly-toxic organotin compound must be used, and a severe deoxygenation step is required to enhance synthesis yield. Thus, the Stille coupling-based method is also unsuitable for large-scale production. In the aforementioned convergent method, building blocks serving as branch portions of repeating units are formed exclusively of 2,3-dibromothiophene, thereby limiting the dendritic structure. Except for the aforementioned dendrimers having thienylene skeleton structural repeating units and synthesis methods therefor, no other such dendrimers and synthesis methods therefor have been known.

Japanese Patent No. 3,074,277 discloses a hyperbranched polymer having thienylene-phenylene units serving as structural repeating units.

However, since the polymer is produced through polymerization based on Grignard reaction, highly regulated repeating structures such as those possessed by dendrimers cannot be provided. Therefore, the compounds synthesized through the Grignard-based method exhibit a broad molecular distribution profile, as conventional polymers exhibit, and functional groups are introduced at random into a core (center moiety) and end moieties (outer end portions), thereby failing to impart desired functions to the polymers.

DISCLOSURE OF THE INVENTION

In view of the foregoing, an object of the present invention is to provide a method for producing a novel dendrimer having a thienylene moiety on the basis of the "convergent method," the method enabling to synthesize the dendrimer having few defects at higher efficiency in a comparatively simple manner. Another object of the invention is to provide a building block compound therefor. Still another object of the invention is to provide a method for producing a thiophene compound.

The present inventors have found that a novel dendrimer having a thienylene moiety can be synthesized on the basis of the "convergent method," which provides a dendrimer having few defects with high efficiency, through repeated employment of reaction steps including converting α-position hydrogen of the thiophene ring to an active group and linking the active group to another compound via Suzuki cross-coupling reaction. The present invention has been accomplished on the basis of this finding. The aforementioned problems involved in Grignard reaction and Stille coupling reaction can be solved through employment of Suzuki cross-coupling reaction. Conventionally, the "convergent method" includes providing a building block having two or more reactive groups and one masked reactive group; causing groups serving as end moieties of the dendrimer to react with the building block; deprotecting the masked reactive group; and causing another compound to react with the building block. However, the above-characterized method of the present invention is an advantageous method and is different from the conventional "convergent method," in that reaction steps are simplified by eliminating a masking step. The present inventors have also found that, in Suzuki cross-coupling reaction, a thiophene organic boron compound having a boron-substituting group serving as an active group is gradually added in a continuous or intermittent manner to a reaction system containing a reactive compound having a substituent (e.g., halogen) serving as a reaction counterpart, whereby decomposition of the thiophene organic boron compound can be prevented, thereby enhancing the yield of the dendrimer. The present invention has been accomplished also on the basis of this finding. Through employment of the above addition method along with the aforementioned method for producing a dendrimer on the basis of the "convergent method" in combination, synthesis yield of a dendrimer can further be enhanced.

Accordingly, a first mode of the present invention provides a method for producing a dendrimer having a structural repeating unit which is represented by formula (1) and which contains a linear portion including a thienylene moiety and a branch portion Y formed of an optionally substituted trivalent organic group, the method being based on the convergent method, characterized in that the method comprises reaction step 1 of converting α-position hydrogen of the thiophene ring of a thienylene-moiety-containing compound (a) for forming end moieties to an active group $V_1$ which undergoes Suzuki cross-coupling reaction, to thereby form compound (b); reaction step 2 of subjecting a compound (c) to Suzuki cross-coupling reaction with the compound (b), to thereby yield compound (d), the compound (c) having a linear portion and a branch portion Y and having, at the branch portion Y, two active groups $V_2$ which undergo Suzuki cross-coupling reaction with the active group $V_1$; reaction step 3 of converting α-position hydrogen of the thiophene ring of the thus-formed compound to an active group $V_1$ which undergoes Suzuki cross-coupling reaction, and reacting the compound (c) with the active group $V_1$, to thereby form a dendron of a subsequent generation; and a step of repeating the reaction step 3 in accordance with needs, to thereby form a dendrimer:

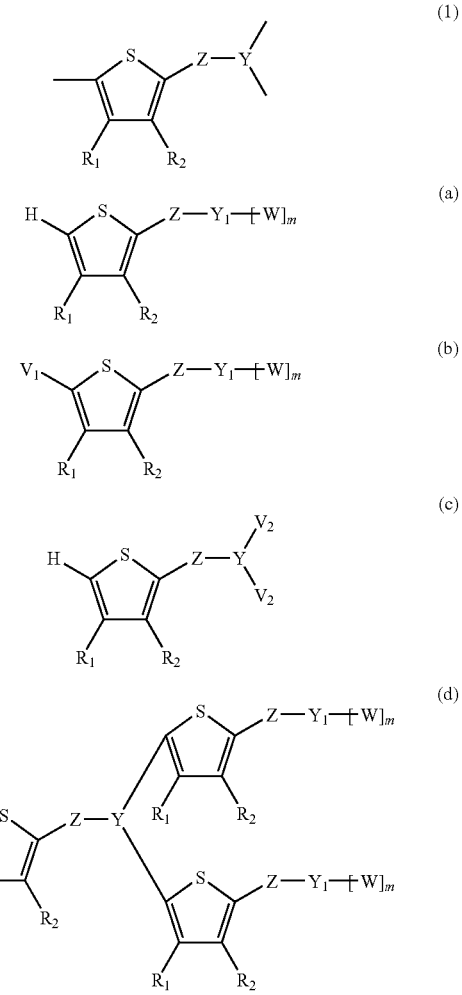

(wherein Z represents a single bond or an optionally substituted divalent organic group having no active group; each of $R_1$ and $R_2$ is selected from among a hydrogen atom, an alkyl group, and an alkoxy group; Y represents an optionally substituted trivalent organic group; $Y_1$ is identical to Y or represents an organic group having a skeleton identical to that of Y; W may be absent or represents an optionally substituted monovalent organic group having no active group; m is an integer of 0 or more; and each of $V_1$ and $V_2$ serving as active groups is selected from active groups which undergo Suzuki cross-coupling reaction, $V_1$ and $V_2$ being able to be mutually cross-coupled).

A second mode of the present invention is drawn to a specific embodiment of the method for producing a dendrimer of the first mode, wherein the active group $V_1$ is selected from the following group 1 and the active group $V_2$ is selected from the following group 2.

Group 1

—B(OH)$_2$    —B(OR)$_2$

R = methyl, ethyl, isopropyl, or butyl

-continued

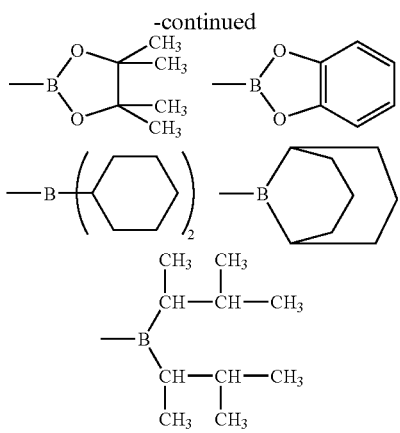

group 2

Cl, Br, I, OSO$_2$(C$_k$F$_{2k+1}$)

K = 1 to 4

A third mode of the present invention is drawn to a specific embodiment of the method for producing a dendrimer of the first mode, wherein the active group V$_1$ is selected from the following group 3 and the active group V$_2$ is selected from the following group 4.

Group 3

Cl, Br, I

Group 4

—B(OH)$_2$    —B(OR)$_2$

R = methyl, ethyl, isopropyl, or butyl

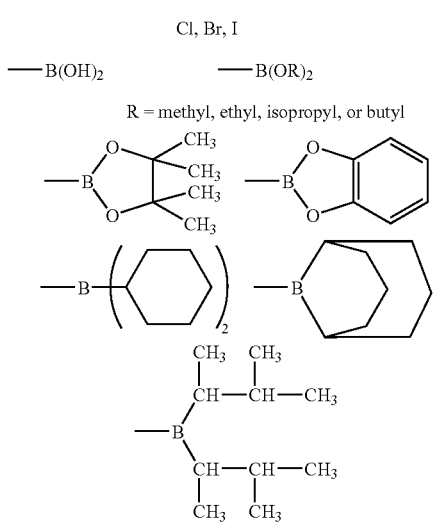

A fourth mode of the present invention is drawn to a specific embodiment of the method for producing a dendrimer of any of the first to third modes, wherein, in the case where a compound used in the Suzuki cross-coupling reaction is a thiophene organic boron compound containing boron, the thiophene organic boron compound is gradually added in a continuous or intermittent manner to a reaction system containing the other counterpart compound, thereby performing Suzuki cross-coupling reaction.

A fifth mode of the present invention is drawn to a specific embodiment of the method for producing a dendrimer of any of the first to fourth modes, which further includes a reaction step of converting α-position hydrogen of the thiophene ring of a compound (e) produced through singly or repeatedly carrying out the reaction step 3 to an active group V$_1$, to thereby form a compound (f); and a reaction step of reacting the compound (f) with a compound (g) having Y$_2$ serving as a core, to thereby form a compound represented by

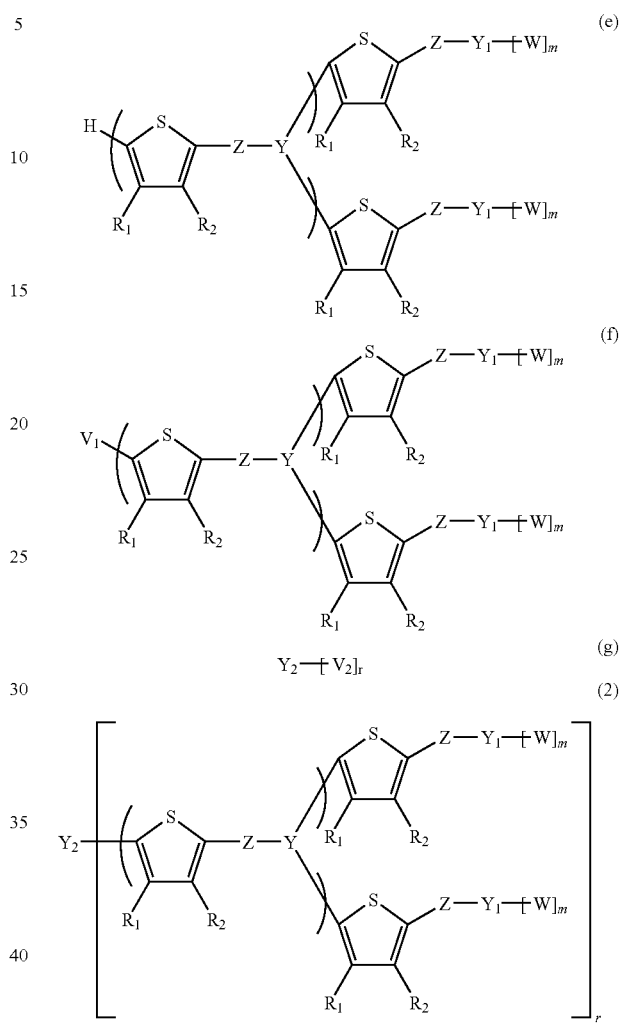

(wherein Y$_2$ represents an r-valent organic group, and r is an integer of 1 or more).

A sixth mode of the present invention provides a compound serving as a building block employed in a method for producing a dendrimer on the basis of a convergent method, the dendrimer having a structural repeating unit including a thienylene moiety, characterized in that the compound is represented by formula (I-1):

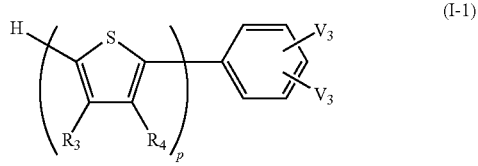

(I-1)

(wherein p is an integer of 1 to 10; each of R$_3$ and R$_4$ is selected from among a hydrogen atom, an alkyl group, and an alkoxy group; when p is 2 to 10, R$_3$ and R$_4$ in each thienylene structural repeating unit may be different from each other; and V$_3$ is selected from the following group 5.

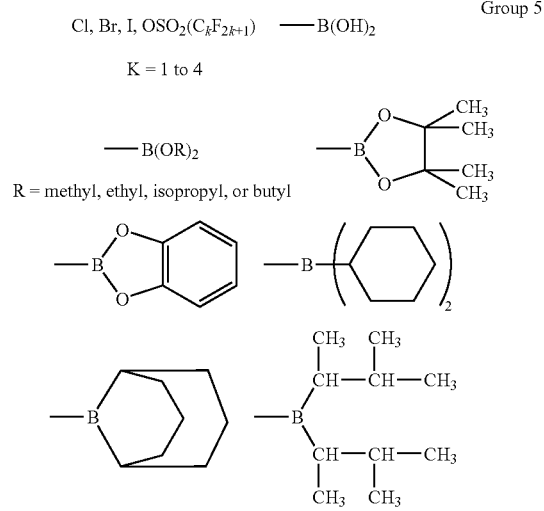

A seventh mode of the present invention provides a compound characterized by being represented by formula (I-2):

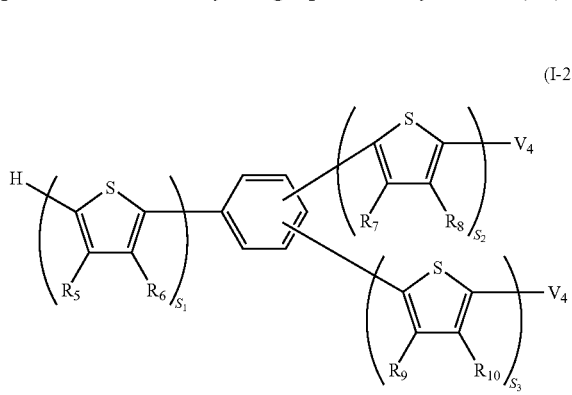

(wherein each of $S_1$ to $S_3$, which may be identical to or different from each other, is an integer of 1 to 10; each of $R_5$ to $R_{10}$ is selected from among a hydrogen atom, an alkyl group, and an alkoxy group, and $R_5$ to $R_{10}$ in each thienylene structural repeating unit may be different from one another; and $V_4$ is selected from the following group 6.

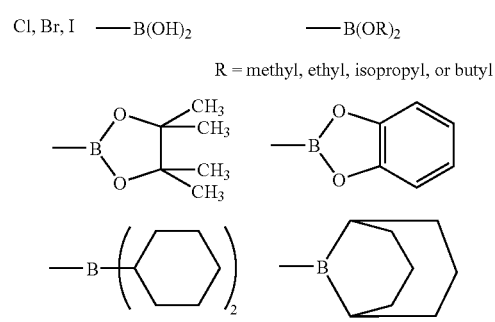

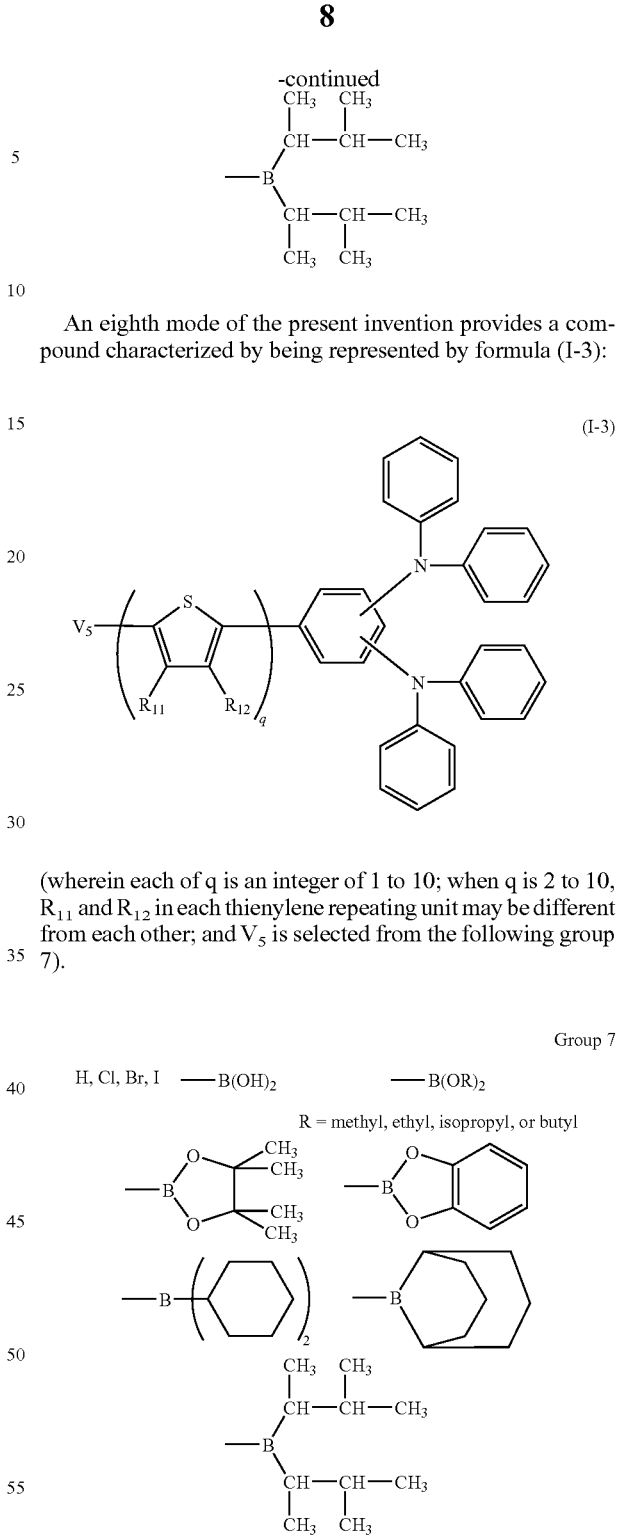

An eighth mode of the present invention provides a compound characterized by being represented by formula (I-3):

(wherein each of q is an integer of 1 to 10; when q is 2 to 10, $R_{11}$ and $R_{12}$ in each thienylene repeating unit may be different from each other; and $V_5$ is selected from the following group 7).

A ninth mode of the present invention provides a method for producing a thiophene compound comprising performing Suzuki cross-coupling reaction between a thiophene organic boron compound and a reactive compound, to thereby form a thiophene compound, characterized in that the thiophene organic boron compound is gradually added in a continuous or intermittent manner to a reaction system containing the reactive compound, thereby performing Suzuki cross-coupling reaction.

A tenth mode of the present invention is drawn to a specific embodiment of the method for producing a thiophene compound of the ninth mode, wherein the thiophene organic boron compound has an active group $V_6$ selected from the following group 1 and the reactive compound has an active group $V_7$ selected from the following group 2.

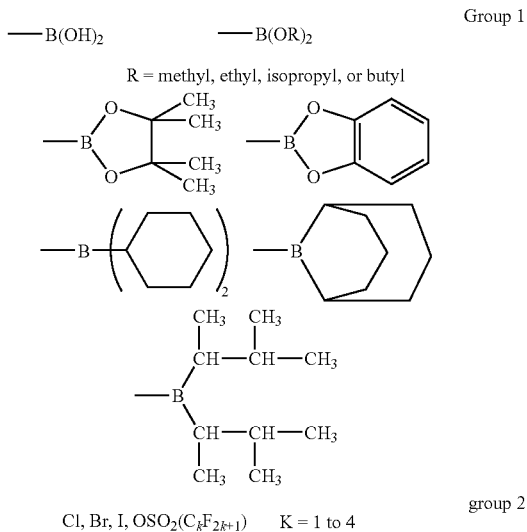

BEST MODES FOR CARRYING OUT THE INVENTION

The present invention will next be described in detail.

The term "dendrimer" produced according to the present invention conceptually refers to generally defined dendrimers which are produced through the convergent method known as a dendrimer synthesis method and excludes hyperbranched polymers synthesized through a typical polymerization method. Thus, the dendrimer encompasses any compounds having a structure in which the aforementioned structural repeating unit represented by formula (1) (i.e., dendritic structural unit) is repeated once or more. Notably, a structure including the aforementioned structural repeating unit represented by formula (1); i.e., a structure including the repeating units which have been repeated so as to form a divergent structure, is referred to as a "branching structure."

Dendrimers and hyperbranched polymers are generally represented by the following structural formulas. As shown in the formulas, the dendrimer has a regularly repeated branching structure, while the hyperbranched polymer has an irregularly repeated branching structure. The dendritic polymers produced through the method of the present invention are dendrimers, and the dendrimers may have a structure in which the polymer chains are dendritically branched from one focal point, or a structure in which polymer chains are radiated from a plurality of focal points linked to a polyfunctional molecule serving as a core. Although other definitions of these species may also be acceptable, in any case, the dendrimer produced through the method of the present invention has a regularly repeated branching structure and encompasses dendrimers which may have a dendritically branching structure or a radially branching structure. Needless to say, the dendrimer of the present invention also encompasses dendrimer compounds produced through a conventional convergent method and having defects in a branching structure attributable to the method.

According to a generally accepted definition, when a dendritic structural unit extends from its preceding dendritic structural unit as an exact copy thereof, the extension of the unit is referred to as the subsequent "generation." It should be noted that the definition of a "dendrimer" according to the present invention covers those having a structure in which each of the dendritic structural units which are similar to one another with the same basic structure are repeated at least once also fall within the scope of the present invention.

The concepts in relation to dendrimer, hyperbranched polymer, etc. are described in, for example, Masaaki KAKIMOTO, Chemistry, Vol. 50, p. 608 (1995) and Macromolecules, Vol. 47, p. 804 (1998), and these publications can be referred to and are incorporated herein by reference. However, the descriptions in these publications should not be construed as limiting the present invention thereto.

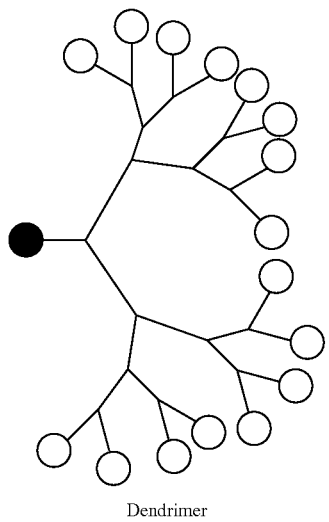

Dendrimer

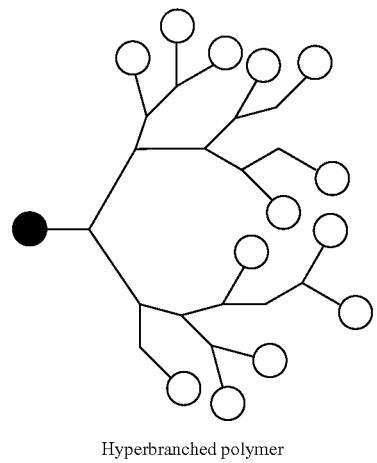

Hyperbranched polymer

● : Focal point
○ : End

-continued

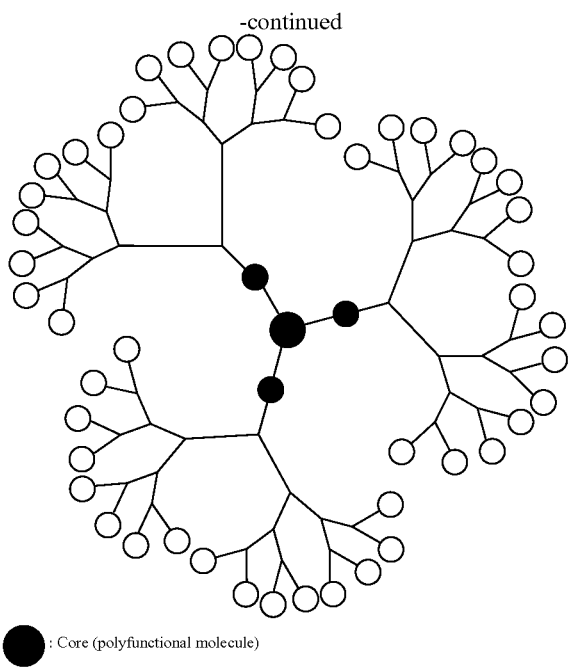

● : Core (polyfunctional molecule)

In the dendrimer produced through the method of the present invention, a dendritic structural unit as shown in the above formula (1) is formed of a linear portion having a thienylene moiety and a branch portion Y which is an optionally substituted trivalent organic group. The structure in which the dendritic structural unit is repeated once to provide a two-stage structure is in fact "a structure in which each of the branch portions Y of that structural unit is bonded to another but identical structural unit." The resultant structure is referred to as a "1st-generation dendron." A similar structure in which dendritic structural units having the same structure are successively linked to the bonding hands of the branch portions Y of a 1st-generation dendron is referred to as a "2nd-generation dendron. In a similar manner, an nth-generation dendron is created. Such dendrons per se and dendrons to which a desired substituent or substituents are bonded to the ends or the focal point thereof are referred to as "dendrimers of dendritically branching structure." When a plurality of dendritically branched dendrimers, which are identical to or different from one another, are bonded as subunits to a multivalent core, the formed dendritic polymer is called "dendrimer of radially branching structure."

In the compounds represented by formulas (e), (f), or (2), the dendritic structural unit enclosed by parentheses; i.e., the structure represented by formula (h), represents a regularly controlled or not completely regularly controlled dendritic branching structure in which the dendritic structural unit is repeated arbitrary times. Thus, in the compounds represented by formulas (e), (f), or (2), if the number of repetitions of a branch structure is n, the formed dendrimer is of the nth-generation. However, the expression "nth-generation" is merely an exemplary appellation, and the compounds are not necessarily limited to those referred to as the "nth-generation."

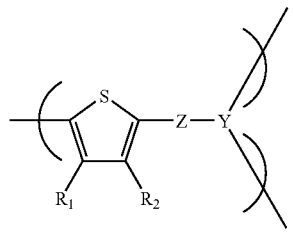

(h)

Specific examples of the dendrimers produced through the method of the present invention include the compounds represented by the following formula:

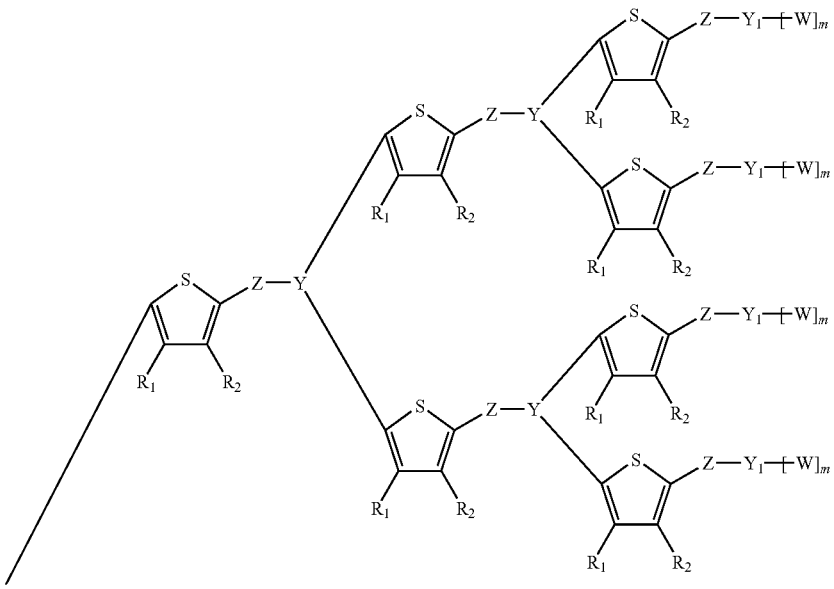

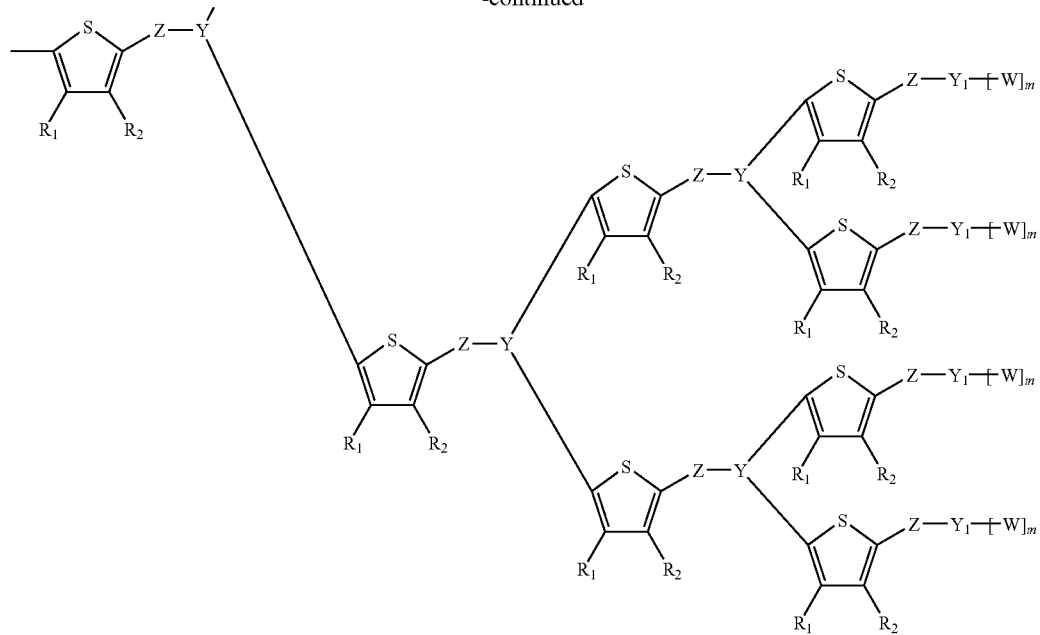

wherein the branch portion Y is a trivalent group, and each of the two bonds except the bond connecting to Z is linked to an atom or a group, and two atoms or groups may be a common species or different species.

$Y_1$ is identical to Y or represents an organic group having a skeleton identical to that of Y. The expression "$Y_1$ is identical to Y or represents an organic group having a skeleton identical to that of Y" refers to that $Y_1$ at least includes, on the Z-bonding side thereof, a structure identical to Y or a structure having a skeleton identical to that of Y. For example, when Y linking to Z is a moiety represented by formula (A), $Y_1$ is a moiety represented by formula (B), (C), (D), etc.:

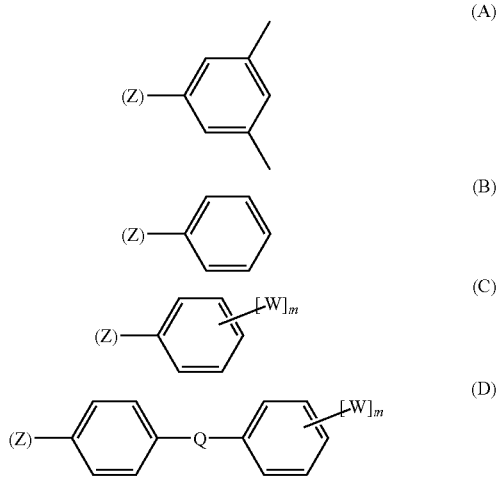

(wherein m is an integer of 1 to 5; and Q is an arbitrary substituent).

No particular limitation is imposed on the number of branch points contained in the dendrimer produced through the method of the present invention.

The present invention is directed to a method for producing a dendrimer having a dendritic structural unit which is represented by formula (1) and which contains a linear portion including a thienylene moiety and a branch portion Y, the linear portion being a divalent organic group containing at least one thienylene moiety, wherein the method comprises reaction steps represented by the following scheme (I) and reaction step 3 repeated in accordance with needs, to thereby form a dendron of a desired generation. In the following formulas, each of $V_1$ and $V_2$ is an active group which undergoes Suzuki cross-coupling, Z represents a single bond or an optionally substituted divalent organic group having no active group; and each of $R_1$ and $R_2$ is selected from among a hydrogen atom, an alkyl group, and an alkoxy group. In the present specification, unless otherwise specified, the alkyl group, the alkoxy group, or a similar group has 1 to 20 carbon atoms. Y represents an optionally substituted trivalent organic group, and $Y_1$ is identical to Y or represents an organic group having a skeleton identical to that of Y. W may be absent or represents an optionally substituted monovalent organic group having no active group, and m is an integer of 0 or more.

Reaction scheme (I)

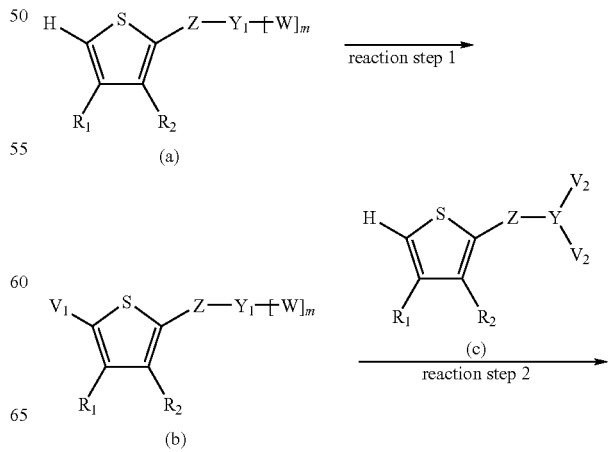

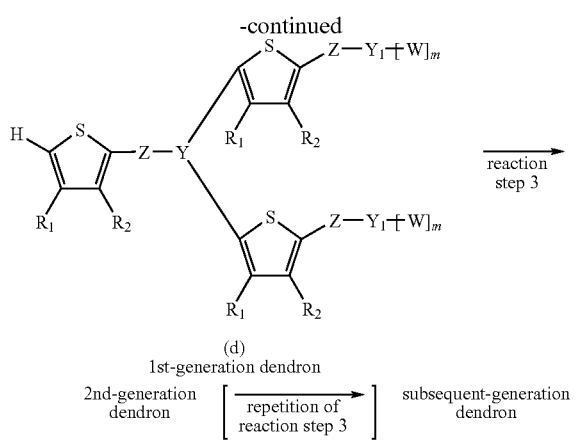

(d)
1st-generation dendron

2nd-generation dendron [repetition of reaction step 3] subsequent-generation dendron The reaction steps represented by the scheme (I) include reaction step 1 of converting α-position hydrogen of the thiophene ring to an active group $V_1$; reaction step 2 of linking $V_1$ and $V_2$ through Suzuki cross-coupling reaction, to thereby increase generation; reaction step 3 of converting α-position hydrogen of the thiophene ring of the compound (d) produced in the reaction step 2 to an active group $V_1$ and reacting compound (c) with the active group $V_1$ so as to further increase generation; and a step of repeating the reaction step 3 in accordance with needs. W serves as an end moiety of the produced dendrimer.

In the scheme (I), the aforementioned compound represented by formula (I-1) or (I-2) is preferably employed in the reaction step 2 as the compound (c) serving as a building block for forming a dendrimer. No particular limitation is imposed on the method for synthesizing the compounds represented by formula (I-1) or (I-2), and these compounds may be synthesized through combination of a coupling reaction between the corresponding thiophene derivative and a benzene derivative and introduction of a halogen atom or a boron-containing substituent serving as an active group. Although Grignard reaction and Stille coupling reaction may be employed as a coupling reaction, Suzuki cross-coupling is preferably employed, similar to the production method of the present invention.

In the reaction scheme (I), no particular limitation is imposed on the method of synthesizing compound (a) serving as a starting material in reaction step 1. The compound (a) may be produced through a reaction step represented by the following reaction scheme (II) in which W for forming end moieties is bonded to $Y_1$ through reaction with $V_1$ and $V_2$.

Reaction scheme(II)

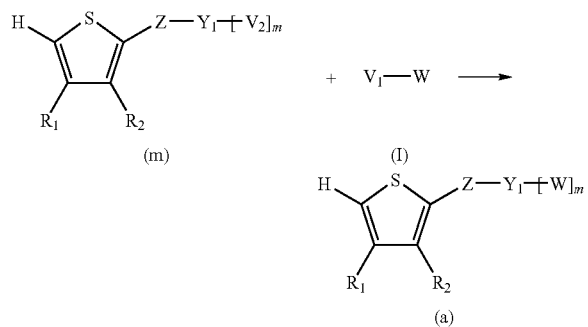

When triarylamine skeletons—hole conductive material—are introduced to branch ends, a compound represented by the above formula (I-3) is preferably employed as the compound (a). No particular limitation is imposed on the method of producing the compound. In one preferred approach, when benzene nucleus is employed as $Y_1$ and the compound in which $V_2$ is a halogen and $V_1$—W is a secondary arylamine compound represented by the following formula is employed in the reaction scheme (II), the above triarylamine skeletons can be synthesized through condensation reaction.

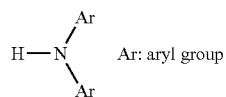

The condensation reaction can be performed through, for example, Ullmann condensation (see Chem. Lett., 1145, (1989), Synth. Commu. 383, (1987), etc.) employing copper and a base catalyst, or the Tosoh method (Japanese Patent Application Laid-Open (kokai) No. 10-310561) employing a palladium catalyst-tri-t-butylphosphine ligand and a base catalyst. Of these, the Tosoh method is preferred, since reaction can be performed under mild conditions and high yield and selectivity can be attained. Through employment of the reaction, triarylamine skeletons are introduced through, for example, the following reaction scheme.

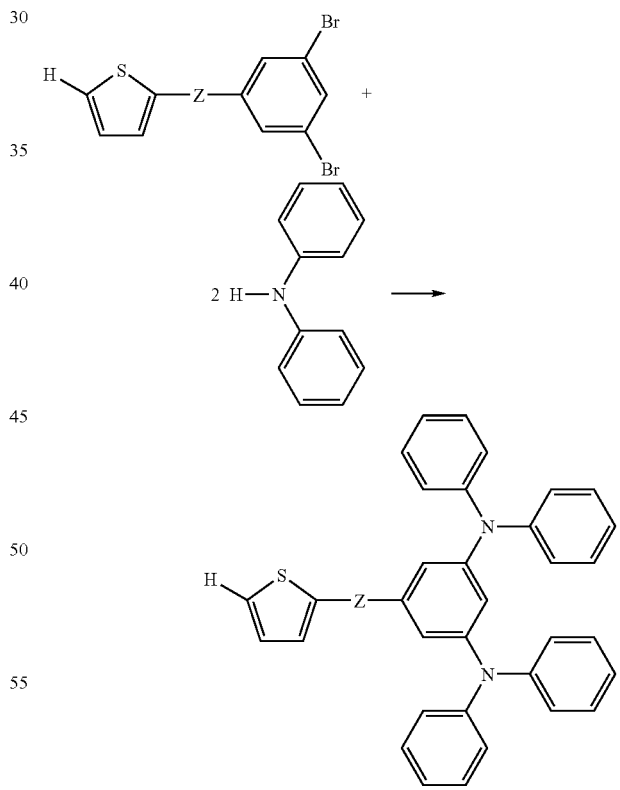

A compound represented by the above formula (I-1) is preferably employed as the compound (m) in the reaction scheme (II).

In the reaction scheme (I) or (II), the reaction between $V_1$ and $V_2$ is performed through Suzuki cross-coupling. Suzuki cross-coupling reaction is known to impose few limitations on functional groups to be employed, to provide high selectivity of reaction, and to cause few side reactions such as homo-coupling, and is particularly employed for a wide range of cross-coupling reactions of aromatic compounds and vinyl compound derivatives (see Suzuki et al., Yuki Gosei Kagaku Kyokai Shi, 46, 848, (1988), Suzuki et al., Chem. Rev., 95, 2457 (1995), and Suzuki, J. Organomet. Chem., 576, 147 (1999)). Therefore, according to the production method of the present invention, the dendrimer can be formed from a wide variety of skeletons.

In the aforementioned reaction scheme (I) or (II), $V_1$ and $V_2$ are groups which are reacted with each other via Suzuki cross-coupling. Combinations of substituents $V_1$ and $V_2$ in each reaction step can be selected individually. Examples of preferred combination will be described next.

In a first exemplified combination of $V_1$ and $V_2$, $V_1$ is selected from the aforementioned group 1 and $V_2$ is selected from the aforementioned group 2. Combinations of $V_1$ (boronic acid ester substituent; $B(OH)_2$ or $B(OR)_2$) and $V_2$ (Br or I) are preferably employed, from the viewpoint of high yield and selectivity, applicability, etc. In this case, Y in the aforementioned reaction scheme is a trivalent organic group which may have a substituent, and examples of the trivalent organic group include those having a moiety to be linked to $V_2$ (e.g., structures such as allyl, alkenyl, alkynyl, benzyl, aryl, and alkyl, and heterocycle-containing structures). W serving as end groups of the dendrimer may be absent or represents an optionally substituted monovalent organic group having no active group. As used herein, the expression "having no active group" means that W contains no group participating Suzuki cross-coupling reaction. Examples of W include an aryl group, an alkenyl group, and an alkyl group, which may be substituted or non-substituted.

In a second exemplified combination, $V_1$ is selected from the aforementioned group 3 and $V_2$ is selected from the aforementioned group 4. In this case, Y in the aforementioned reaction scheme is a trivalent organic group which may have a substituent, and examples of the trivalent organic group include those having a moiety to be linked to $V_2$ (e.g., structures such as aryl, alkenyl, and alkyl, and heterocycle-containing structures). W serving as end grouts of the dendrimer may be absent or represents an optionally substituted monovalent organic group having no active group. As used herein, the expression "having no active group" means that W contains no group participating Suzuki cross-coupling reaction. Examples of W include an allyl group, an alkenyl group, an alkynyl group, a benzyl group, an aryl group, and an alkyl group, which may be substituted or non-substituted.

In the aforementioned first and second combinations, Y is a trivalent organic group; $Y_1$ is identical to Y or represents an organic group having a skeleton identical to that of Y; and Z is a single bond or an optionally substituted divalent organic group having no active group. As used herein, the expression "having no active group" means that that Z contains no group participating Suzuki cross-coupling reaction. Notably, in the case of the first combination, a reaction step in which an active group is introduced through halogenation can be eliminated. Thus, the first combination is also preferably employed in the case where a skeleton or substituent which is active to a halogenating agent is present in addition to target active-group-introduction sites.

Examples of preferred X and Y (X represents -thiophene ring-Z-) include the following:

Y:

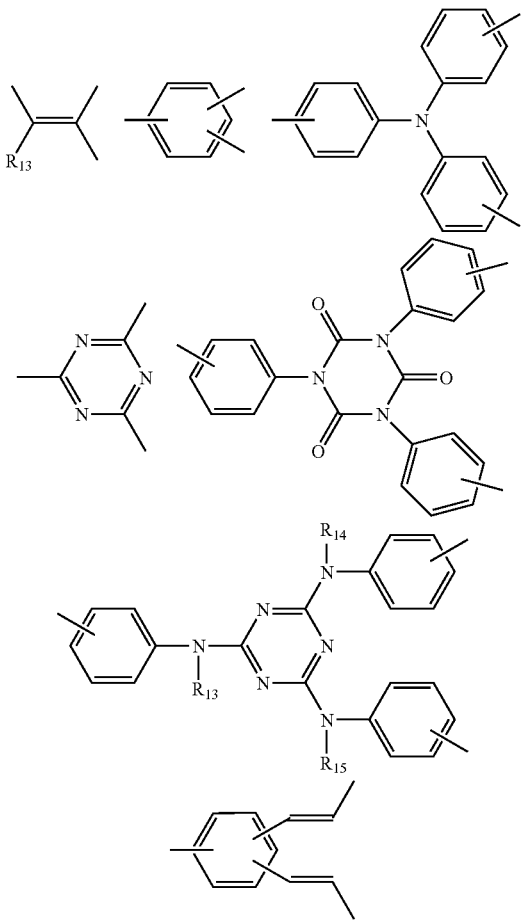

$R_{13}$, $R_{14}$, $R_{15}$ = a hydrogen atom or an alkyl group

X:

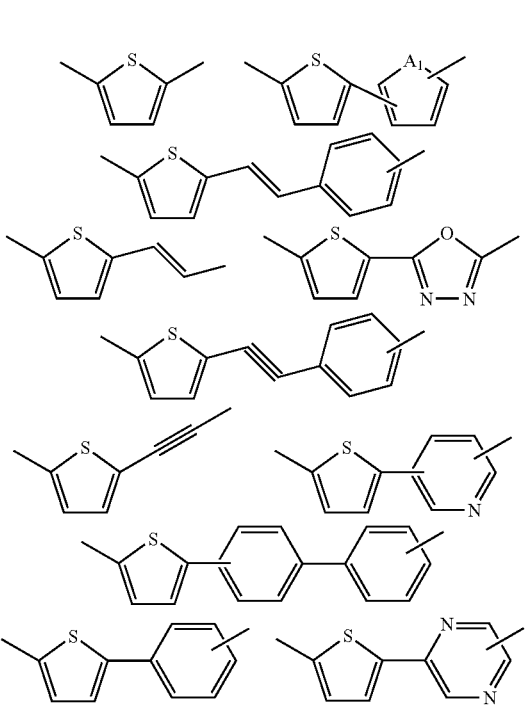

-continued
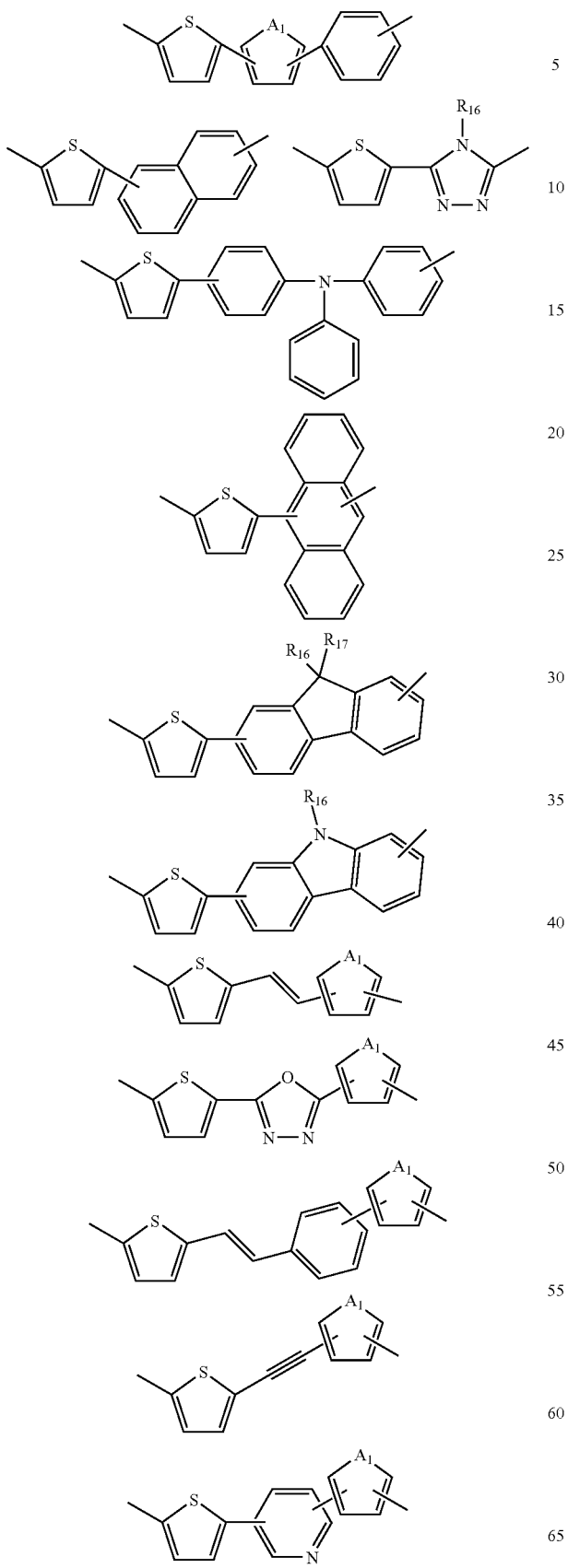
-continued
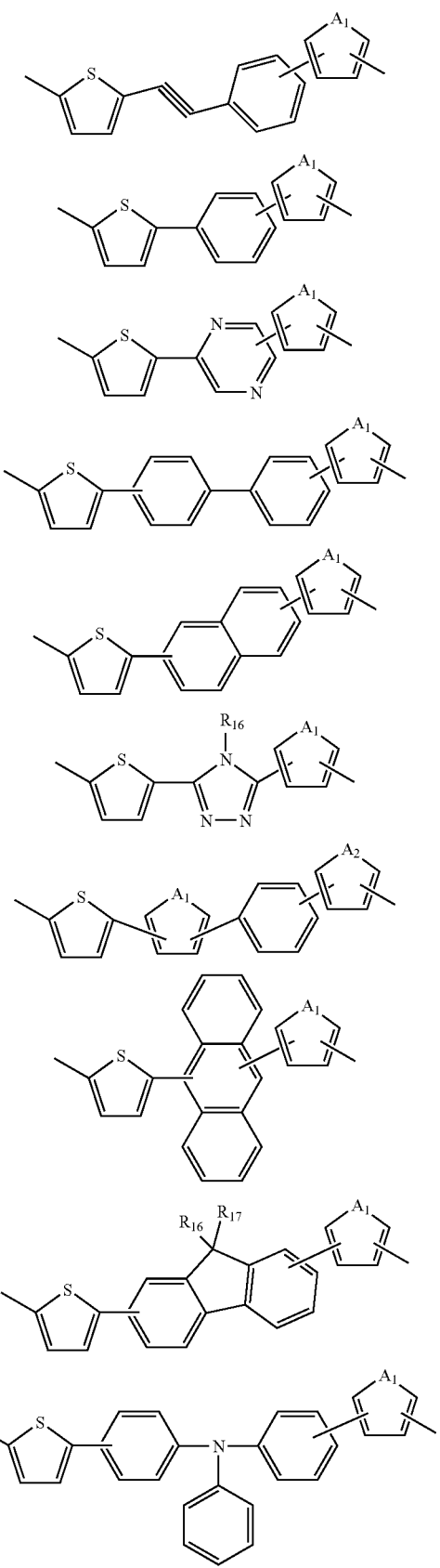

-continued

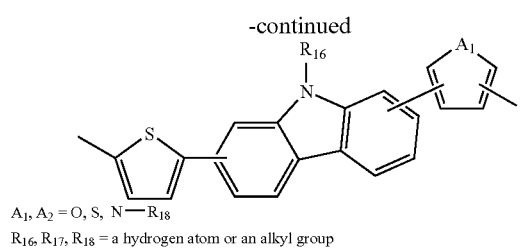

A$_1$, A$_2$ = O, S, N—R$_{18}$
R$_{16}$, R$_{17}$, R$_{18}$ = a hydrogen atom or an alkyl group Notably, if each Y and Z is at least partially conjugated with thienylene, the produced dendrimer becomes semiconductive. As used herein, the expression "at least partially conjugated with" refers not only to the case where a perfect conjugated system is established, but also to the case where not all the electrons of the π-electron systems are ubiquitously present. For example, a conjugated system containing an m-substituted benzene nucleus also falls within the meaning of this definition.

Exemplary reaction conditions under which conversion of α-position hydrogen of the thiophene ring to active group V$_1$ and reaction of active groups V$_1$ and V$_2$ are performed will next be described.

[Conversion of α-Position Hydrogen of the Thiophene Ring to Active Group V$_1$]

Exemplary reaction conditions employed in reaction steps 1 and 3 for converting α-position hydrogen of the thiophene ring to active group V$_1$ selected from Group 1 will be described.

When V$_1$ is formed from B(OR)$_2$ or the boronic acid ester represented by the following formula, α-position hydrogen of the thiophene ring is drawn through the action of alkyllithium (e.g., n-butyllithium), lithium diisopropylamide, etc., to thereby form the corresponding carbanion, and subsequently, the corresponding alkoxyborane (i.e., trimethoxyborane, triethoxyborane, triisopropoxyborane, tributoxyborane, or 2-isopropoxy-4,4,5,5-tetramethyl-1,3,2-dioxaborolane) is electrophilically added to the carbanion.

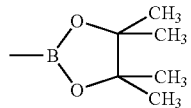

Examples of preferably employed solvents include organic solvents such as tetrahydrofuran, n-hexane, diethyl ether, and toluene. The reactions are preferably performed for 10 minutes to three hours at −100 to 30° C., more preferably for 30 minutes to two hours at −78 to 0° C.

When V$_1$ is formed from B(OH)$_2$, any of the boronic acid esters obtained in the above manner is hydrolyzed through addition of water. Although no particular limitation is imposed on the reaction solvent, water is directly added to the reaction mixture yielded upon synthesis of a boronic acid ester in the above manner, to thereby perform hydrolysis. The addition of water is convenient for production. The reaction is preferably performed for one hour to three hours at 0 to 50° C.

Exemplary reaction conditions employed in reaction steps 1 and 3 for converting α-position hydrogen of the thiophene ring to active group V$_1$ selected from the abovementioned Group 3 will be described.

When V$_1$ is formed from any of Cl, Br, and I, the corresponding halogenating reagent is reacted, to thereby convert α-position hydrogen of the thiophene ring to halogen. Examples of halogenating agents include N-chlorosuccinimide, N-bromosuccinimide, and N-iodosuccinimide. Examples of preferably employed reaction solvents include organic solvents such as tetrahydrofuran, n-hexane, diethyl ether, benzene, carbon tetrachloride, carbon disulfide, dimethylformamide, and acetic acid. The reaction is preferably performed for one hour to 24 hours at −20 to 80° C.

[Reaction of Active Group V$_1$ and Active Group V$_2$]

Exemplary reaction conditions employed in reaction steps 2 and 3 for reacting V$_1$ and V$_2$ through Suzuki cross-coupling will be described.

When Suzuki cross-coupling is performed, a variety of combinations of palladium catalysts and base catalysts can be employed.

Examples of palladium catalysts include tetrakis(triphenylphosphine)palladium, palladium acetate, palladium chloride, palladium black, bis(triphenylphosphine)palladium dichloride, bis(tri-o-tosylphosphine)palladium dichloride, bis(dibenzylideneacetone)palladium, bis(tricyclohexylphosphine)palladium dichloride, bis(triphenylphosphine)palladium diacetate, [1,2-bis(diphenylphosphino)butane]palladium dichloride, and [1,2-bis(diphenylphosphino)ethane]palladium dichloride. In addition, combination of a ligand compound with these palladium catalysts may be effective. Examples of ligand compounds include triphenylphosphine, 1,1'-bis(diphenylphosphino)ferrocene, 1,2-bis(diphenylphosphino)ethane, 1,3-bis(diphenylphosphino)propane, 1,4-bis(diphenylphosphino)butane, sodium diphenylphosphinobenzene-3-sulfonate, tricyclohexylphosphine, tri(2-furyl)phosphine, tris(2,6-dimethoxyphenyl)phosphine, tris(4-methoxyphenyl)phosphine, tris(4-methylphenyl)phosphine, tris(3-methylphenyl)phosphine, and tris(2-methylphenyl)phosphine. Instead of palladium catalysts, nickel catalysts including [1,1'-bis(diphenylphosphino)ferrocene]nickel dichloride, bis(tricyclohexylphosphino)nickel dichloride, and nickel chloride hexahydrate may also be used.

Examples of base catalysts include sodium carbonate, sodium alkoxides (e.g., sodium ethoxide), potassium t-butoxide, barium hydroxide, triethylamine, potassium phosphate, sodium hydroxide, and potassium carbonate.

When Suzuki cross-coupling reaction is performed, any of a variety of organic solvents, mixtures thereof, and mixtures thereof with water is generally used as a solvent. Examples of suitably used organic solvents include dimethylformamide, ethanol, methanol, dimethyl sulfoxide, dioxane, benzene, toluene, tetrahydrofuran, dimethoxyethane, dimethylacetamide, xylene, 1-propanol, 2-propanol, 2-methyl-1-propanol, 2-methyl-2-propanol, 1-butanol, 2-butanol, acetone, 2-butanone, 3-methyl-2-butanone, 2-pentanone, 3-pentanone, 4-methyl-2-pentanone, 2-methyl-3-pentanone, 2,4-dimethyl-3-pentanone, dioxolan, N-methylpyrrolidone, diethoxyethane, ethylene glycol, ethylene glycol monomethyl ether, ethylene glycol monoethyl ether, ethylene glycol ethyl methyl ether, diethylene glycol, diethylene glycol monomethyl ether, diethylene glycol monoethyl ether, diethylene glycol dimethyl ether, diethylene glycol diethyl ether, diethylene glycol ethyl methyl ether, mesitylene, ethylbenzene, anisole, nitrobenzene, and tetramethylurea. The coupling reaction is performed preferably for 30 minutes to 24 hours at 25 to 150° C., more preferably for one hour to 12 hours at 25 to 80° C.

The same reaction conditions as employed in the aforementioned reaction steps 2 and 3 can be applied to the reaction conditions under which the reaction step represented by the reaction scheme (II); i.e., linking W serving as end moieties to Y$_1$ through reaction between V$_1$ and V$_2$, thereby producing the compound (a) serving as a starting material in the reaction step 1.

In one alternative procedure, a dendritic structure of a desired generation is grown through the reaction step 3 or repetition of the reaction step 3 and the thus-produced structure may be linked to a core, thereby producing a dendrimer represented by formula (2). In formula (2), $Y_2$ represents an r-valent organic group (r is an integer of $\geq 1$), and the "r" of compound (2) refers to the number of branches generating from the center moiety. If r is 2 or more, the dendrimer has a radially branching structure, whereas when r is 1, a dendrimer of a dendritically branching structure is formed. In the present invention, $Y_2$ of this type of dendrimer is also referred to as a "core."

Specifically, as shown in the following reaction scheme (III), a compound represented by formula (e) is formed through the reaction step 3 or repetition of the reaction step 3, and α-position hydrogen of the thiophene ring of the compound (e) is converted to an active group $V_1$, to thereby form a compound (f). The compound (f) is reacted with a compound (g) having $Y_2$ serving as a core. In these reactions, the same manners and conditions as employed in the aforementioned reaction steps 1 to 3 are applied to conversion of α-position hydrogen of the thiophene ring to an active group $V_1$ and reaction between $V_1$ and $V_2$.

Reaction scheme (III)

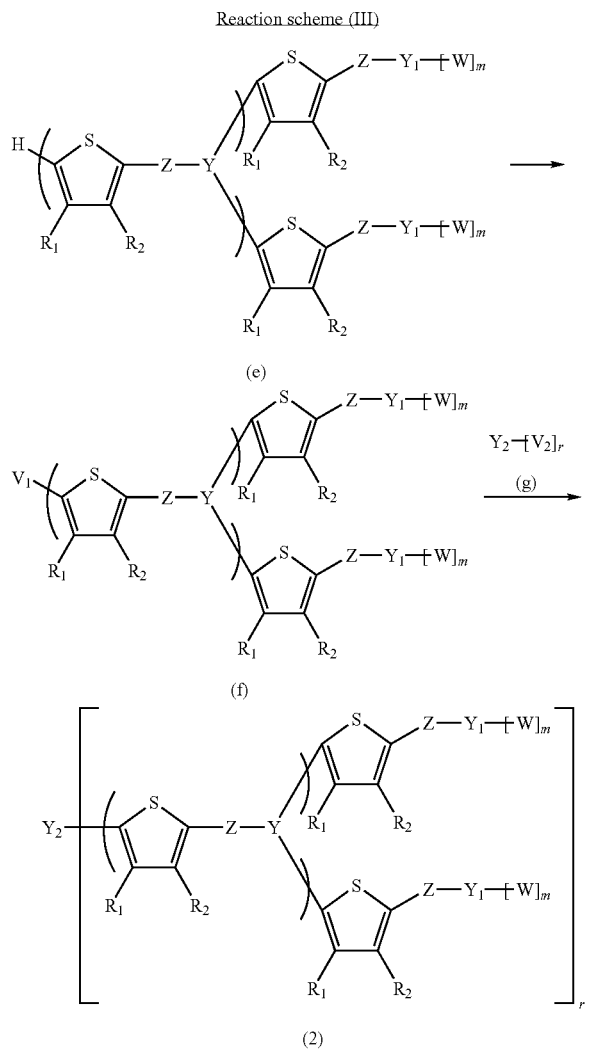

Through the above reactions, a dendrimer of any generation can be linked to a center moiety molecule through the same reaction steps. However, the number of generations of dendrimers is preferably 1 to 10, more preferably 1 to 8, further more preferably 1 to 7, most preferably 2 to 5, from the viewpoint of spatial density of dendritic structural units and easiness of synthesis. The number of branches from the center moiety is preferably 1 to 6, more preferably 1 to 4.

Into the outermost end portions of the dendrimer, a new structure can be introduced through chemical modification of end groups Ws, in the course of growth to increase the generation to a desired number or after completion of linking to a core.

A high-purity dendrimer having few defects can be synthesized by performing purification after completion of each of the aforementioned steps. No particular limitation is imposed on the purification method, and examples include recrystallization, crystallization, purification with sublimation, and purification by use of a column.

According to the production method of the present invention, a variety of dendrimers can be produced through appropriate selection of the compound (a) forming end moieties, the compound (c) serving as a monomer unit of the dendritic structure, and the compound (g) serving as a center moiety. In addition, since the present invention employs the "convergent method," in which purification after completion of each reaction step can be readily performed, a high-purity dendrimer having few defects can be produced.

The present inventors have found, in the Suzuki cross-coupling reaction between a thiophene organic boron compound and a reactive compound employed in the aforementioned method for producing a dendrimer, that the thiophene organic boron compound is susceptible to hydrolysis in the reaction system, and that decomposition of the thiophene organic boron compound can be prevented by gradually adding the thiophene organic boron compound in a continuous or intermittent manner to the reaction system containing the reactive compound, thereby preferentially proceeding the Suzuki cross-coupling reaction. In other words, in the production of a thiophene compound through Suzuki cross-coupling reaction between a thiophene organic boron compound and a reactive compound, the thiophene organic boron compound is gradually added in a continuous or intermittent manner to the reaction system containing the reactive compound for Suzuki cross-coupling reaction, whereby the thiophene compound can be produced at high yield. As used herein, the term "thiophene compound" refers to a compound having a thiophene ring.

Examples of the thiophene organic boron compound include those having an active group $V_6$ selected from group 1, and examples of the reactive compound include those having an active group $V_7$ selected from group 2.

The cross-coupling reaction will next be described in detail.

In Suzuki cross-coupling reaction, when the essential starting materials are fed in their entire portions to initiate reaction, two reactions proceed competitively: the target reaction cycle; i.e., oxidation addition-transmetallation-reduction elimination in the presence of a base catalyst and a metallic catalyst such as palladium; and hydrolysis of a thiophene organic boron compound. However, if the thiophene organic boron compound is added gradually (e.g., added dropwise) to the reaction system, the as-added boron compound is immediately involved in the target reaction, and the thus-proceeding reaction is considered to prevent hydrolysis, thereby enhancing the yield. The gradual addition technique (e.g., dropwise addition) may be carried out continuously or intermittently. In a specific procedure, all the starting materials other than the thiophene organic boron compound were fed in their entire portions to the reaction system, followed by gradual addition of the thiophene organic boron compound in a continuous or intermittent manner to the reaction system.

In the case where coupling reaction between a compound having a plurality of reactive sites and a thiophene organic boron compound is performed, steric hindrance and electronic effect may lower the reaction rate; and an excessive base may promote hydrolysis. Therefore, the base catalyst may also be gradually added in a continuous or intermittent manner. For example, when the generation of a dendron is increased, a compound having two reactive sites adjacent to each other is employed. Thus, in a first step, a thiophene organic boron compound is gradually added in a continuous or intermittent manner in the presence of a base catalyst in an amount corresponding to one reactive site, and in a second step, the base catalyst is added in an amount corresponding to the other reactive site, followed by gradual addition of the thiophene organic boron compound in a continuous or intermittent manner. Alternatively, the base catalyst and the thiophene organic boron compound may be added simultaneously in a continuous manner.

In a similar manner, highly decomposable compounds other than the thiophene organic boron compound may be gradually added in a continuous or intermittent manner to the reaction system, thereby enhancing the yield.

Next, exemplary reaction conditions will be described.

When a solid-form thiophene organic boron compound is employed, the compound is dissolved in a solvent to form a solution, which is readily added to the reaction system in a continuous manner, whereas when dissolution of the compound in a solvent is difficult, the compound in the solid form or liquid form is added directly to the reaction system. The aforementioned reaction solvent is suitably employed as the above solvent. Unless reaction is affected, a reaction mixture containing an as-prepared thiophene organic boron compound may be used without any further treatment. No particular limitation is imposed on the addition speed in the case of continuous addition, and a time of 15 minutes to five hours is preferred, with 30 minutes to two hours being more preferred. In the case of intermittent addition, no particular limitation is imposed on the amount of addition per operation and the intervals between addition operations. However, the amount to be added in one operation is adjusted to a theoretically required total amount divided by 5 to 50, and the theoretically required total amount of the compound is preferably added in an intermittent manner within a period of time of 15 minutes to 5 hours, more preferably 30 minutes to two hours. The same conditions as employed above are applied to continuous or intermittent addition of a base catalyst. In a preferred manner, the thiophene organic boron compound is added simultaneously with the base catalyst, or prior to addition of the base catalyst. Furthermore, continuous addition and intermittent addition may be combined. For example, in one possible procedure, a thiophene organic boron compound serving as a reactant is continuously added in half the predetermined amount in the presence of a base catalyst in half the predetermined amount; the other half of the base catalyst is added; and the other half of the thiophene organic boron compound is continuously added. The same reaction temperature as described above is also applicable.

When the above addition technique is applied to the method for producing a dendrimer of the present invention, an organic boron compound having a boron-substituting group serving as an active $V_1$ or $V_2$ is gradually added in a continuous or intermittent manner to a reaction system containing a compound having a counter reactive group, a base catalyst, a reaction solvent, and a metallic catalyst. For example, a compound having an active group $V_1$ selected from group 1 is gradually added in a continuous or intermittent manner to a reaction system containing a compound having an active group $V_2$ selected from group 2, thereby performing Suzuki cross-coupling reaction. Alternatively, a compound having an active group $V_2$ selected from group 4 is gradually added in a continuous or intermittent manner to a reaction system containing a compound having an active group $V_1$ selected from group 3, thereby performing Suzuki cross-coupling reaction.

As described above, when the technique in which a thiophene organic boron compound is gradually added in a continuous or intermittent manner to a reaction system is applied to the method for producing a dendrimer of the present invention, a dendrimer of interest can be produced at high yield.

The present invention will next be described with reference to the below-described Examples in relation to the dendrimer, which should not be construed as limiting the invention thereto. Apparatus, etc. employed in measurement are as follows.

$^1$H-NMR: FT-NMR, model JNM-AL400 (400 MHz, product of JEOL), solvent: CDCl$_3$ or DMSO-d$^6$; room temperature, chemical shift reference (0 ppm): tetramethylsilane (TMS).

GPC: HLC-8220 GPC, product of Tosoh Corporation; Column: TSK gel Super HZM-M; Eluent: THF; Detector: UV 254 nm; Measures (weight average molecular weight (Mw), number average molecular weight (Mn), and molecular weight distribution (Mw/Mn)) are reduced to polystyrene as a standard.

SYNTHESIS EXAMPLE 1

Synthesis of 3rd-Generation Dendrimer

SYNTHESIS EXAMPLE 1-1

Synthesis of a Compound (c), 5-(3,5-dibromophenyl)-2,2'-bithiophene, Serving as a Monomer Providing a Dendritic Structure, Represented by the Following Formula

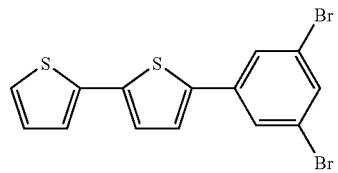

In a nitrogen atmosphere, 2,2'-bithiophene (4.6 g) was dissolved in dehydrated tetrahydrofuran, and the solution was cooled in a dry ice-methanol bath. After cooling, a 1.6M n-butyllithium/hexane solution (18 mL) was added dropwise thereto, and the mixture was allowed to react for one hour. Subsequently, trimethoxyborane (3.4 g) was added dropwise thereto, and the resultant mixture was allowed to react for one hour. After completion of reaction, water was added thereto for hydrolysis. Thereafter, the cooling bath was removed, whereby the temperature of the reaction mixture was elevated to room temperature. An aqueous saturated ammonium chloride solution and diethyl ether were added to the reaction mixture, and the resultant mixture was stirred and left to stand. The formed organic layer was isolated from the mixture, and the aqueous layer was subjected to extraction with a solvent mixture of tetrahydrofuran and diethyl ether (volume ratio: 1/2). The organic layer obtained through extraction was combined with the above organic layer, and the resultant mixture was washed with an aqueous saturated sodium chloride solution. The mixture was dried over sodium sulfate, and the solvent was distilled off under reduced pressure, to thereby yield a crude product. The crude product was recrystallized from tetrahydrofuran/n-hexane, to thereby yield 4.3 g of 2,2'-bithiophene-5-boronic acid (intermediate compound; pale bluish white solid, yield: 73%) represented by the following formula.

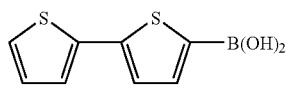

The structure of the obtained product was confirmed through ¹H-NMR spectroscopy. The measurement data are shown below.

¹H NMR (DMSO-d⁶) δ8.30 (s, BOH, 2H), δ7.60 (d, J=3.6 Hz, thiophene ring, 1H), δ7.51 (dd, J=5.2 Hz, J=1.2 Hz, thiophene ring, 1H), δ7.34-7.32 (m, thiophene ring, 2H), δ7.10 (dd, J=5.2 Hz, J=3.6 Hz, thiophene ring, 1H).

Subsequently, in a nitrogen atmosphere, the resultant intermediate compound, 2,2'-bithiophene-5-boronic acid (4.0 g) and 1,3,5-tribromobenzene (9.0 g) were dissolved in tetrahydrofuran. Palladium acetate (0.1 g) and triphenylphosphine (0.30 g) were added thereto, and a solution of sodium carbonate (4.4 g) in water (34 mL) was further added thereto. The mixture was allowed to react for six hours while heating at 80° C. in an oil bath under stirring. After completion of reaction, the temperature of the reaction mixture was lowered to room temperature, and water (30 mL) was added thereto. The resultant mixture was subjected to extraction with methylene chloride, and the formed organic layer was washed with water. The organic layer was dried over sodium sulfate, and the solvent was distilled off under reduced pressure, to thereby yield a crude product. The crude product was isolated and purified through column chromatography (packing material: Silicagel 60 (product of Merck), eluent: methylene chloride/n-hexane), to thereby yield 4.6 g of the target product (pale yellow solid, yield: 61%). The structure of the obtained product was confirmed through ¹H-NMR spectroscopy. The measurement data are shown below.

¹H NMR (CDCl₃) δ7.65 (d, J=11.6 Hz, benzene ring, 2H), δ7.55 (t, J=1.6 Hz, benzene ring, 1H), δ7.26-7.25 (thiophene ring, 1H), δ7.23 (d, J=3.6 Hz, thiophene ring, 1H), δ7.22 (d, J=3.6 Hz, thiophene ring, 1H), δ7.15 (d, J=3.6 Hz, thiophene ring, 1H), δ7.05 (dd, J=5.2 Hz, J=3.6 Hz, thiophene ring, 1H)

SYNTHESIS EXAMPLE 1-2

Synthesis of a Compound (a), 5-[2,2']bithiophenyl-5-yl-N,N,N',N'-tetraphenyl-1,3-phenylenediamine, Forming the Branch ends of a Dendritic Structure, Represented by the Following Formula.

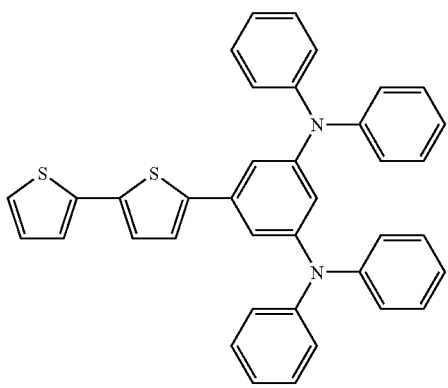

Preparation of Catalyst

Xylene (4.5 mL) was added to palladium acetate (10 mg) and, in a nitrogen atmosphere, tri-t-butylphosphine (36 mg) was added thereto. The mixture was heated at 80° C. for 30 minutes, to thereby prepare a catalyst solution.

Synthesis of 5-[2,2']bithiophenyl-5-yl-N,N,N',N'-tetraphenyl-1,3-phenylenediamine Xylene (4.5 mL) was added to a mixture of 5-(3,5-dibromophenyl)-2,2'-bithiophene (1.80 g) which had been produced in Synthesis Example 1-1, diphenylamine (1.60 g) and potassium t-butoxide (1.21 g), and, in a nitrogen atmosphere, the previously prepared catalyst solution was added dropwise thereto at 80° C. After completion of addition, the reaction mixture was heated to 120° C., and was allowed to react for 18 hours. Subsequently, the temperature of the reaction mixture was lowered to room temperature, and water (10 mL) was added thereto. The formed organic layer was isolated from the mixture, and the aqueous layer was subjected to extraction with methylene chloride. The organic layer obtained through extraction was combined with the above organic layer. The organic layer was dried over sodium sulfate, and the solvent was distilled off under reduced pressure, to thereby yield a crude product. The crude product was isolated and purified through column chromatography (packing material: Silicagel 60 (product of Merck), eluent: methylene chloride/n-hexane), to thereby yield 2.20 g of the target product (pale yellow solid, yield: 85%). The structure of the obtained product was confirmed through ¹H-NMR spectroscopy. The measurement data are shown below.

¹H NMR (CDCl₃) δ7.22 (t, J=7.8 Hz, benzene ring, 8H), δ7.16 (dd, J=1.2 Hz, J=5.2 Hz, thiophene ring, 1H), δ7.11-7.09 (m, thiophene ring, 1H and benzene ring, 8H), δ7.02-6.96 (m, benzene ring, 4H and thiophene ring, 3H), δ6.90 (d, J=2.0 Hz, benzene ring, 2H), δ6.73 (t, J=2.0 Hz, benzene ring, 1H).

SYNTHESIS EXAMPLE 1-3

Synthesis of a Compound (b) 5-(5'-Boronic Acid-[2,2']bithiophenyl-5-yl)-N,N,N',N'-tetraphenyl-1,3-phenylenediamine, Represented by the Following Formula Through Conversion, to Active Group B(OH)₂, of α-position Hydrogen of the Corresponding Thiophene Ring of Compound (a) Forming the Branch Ends of a Dendritic Structure

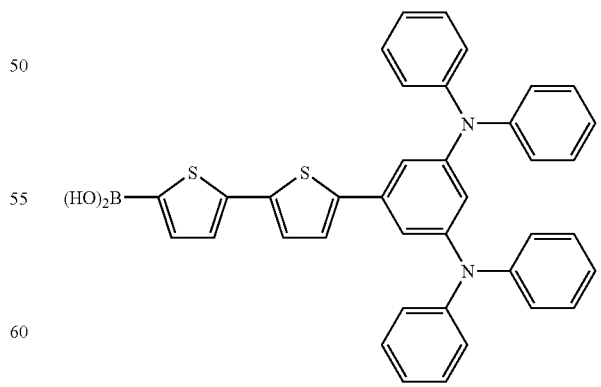

In a nitrogen atmosphere, 5-[2,2']bithiophenyl-5-yl-N,N,N',N'-tetraphenyl-1,3-phenylenediamine (2.0 g) which had been synthesized in Synthesis Example 1-2 was dissolved in dehydrated tetrahydrofuran, and the solution was cooled in a dry ice—methanol bath. After cooling, a 10-wt. % lithium diisopropylamide/n-hexane suspension (4.5 g, product of Aldrich) was added dropwise thereto, and the mixture was allowed to react for one hour. Subsequently, trimethoxyborane (0.5 g) was added dropwise thereto, and the resultant mixture was allowed to react for one hour. After completion of reaction, water was added thereto for hydrolysis. Thereafter, the cooling bath was removed, whereby the temperature of the reaction mixture was elevated to room temperature. An aqueous saturated ammonium chloride solution and diethyl ether were added to the reaction mixture, and the resultant mixture was stirred and left to stand. The formed organic layer was isolated from the mixture, and the aqueous layer was subjected to extraction with a solvent mixture of tetrahydrofuran and diethyl ether (volume ratio: 1/2). The organic layer obtained through extraction was combined with the above organic layer, and the resultant mixture was washed with an aqueous saturated sodium chloride solution. The mixture was dried over sodium sulfate, and the solvent was distilled off under reduced pressure, to thereby yield a crude product. The crude product was recrystallized from tetrahydrofuran/n-hexane; to thereby yield 1.5 g of the target product (pale yellow solid, yield: 70%). The structure of the product was confirmed through $^1$H-NMR spectroscopy (solvent for measurement: DMSO-d$^6$) from the fact that a peak attributed to the OH proton of the boronic acid is observed at about 8.3 ppm and that the ratio of the integrated value of the benzene-ring-originating protons to that of the thiophene-ring-originating protons coincides with that of the target structure product.

SYNTHESIS EXAMPLE 1-4

Synthesis of 1st-generation Dendrimer Represented by the Following Formula (11) Through Suzuki Cross-coupling Reaction of Compound (b) with Compound (c)

wherein, "a" represents the position of proton Ha, on which an integrated value obtained by $^1$H-NMR spectroscopy was evaluated.

<Suzuki Coupling Reaction not Employing Continuous/Intermittent Addition>

In a nitrogen atmosphere, THF (10 mL) and water (2 mL) were added to a mixture of 5-(5'-boronic acid-[2,2']bithiophenyl-5-yl)-N,N,N',N'-tetraphenyl-1,3-phenylenediamine (1.30 g) which had been produced in Synthesis Example 1-3; 5-(3,5-dibromophenyl)-2,2'-bithiophene (0.40 g) which had been produced in Synthesis Example 1-1; palladium acetate (13 mg); triphenylphosphine (46 mg); and sodium carbonate (0.22 g), and the resultant mixture was allowed to react for eight hours under reflux conditions. After completion of reaction, the reaction mixture was cooled to room temperature, and water (20 mL) was added thereto. The resultant mixture was subjected to extraction with methylene chloride, and the formed organic layer was washed with water. The organic layer was dried over sodium sulfate, and the solvent was distilled off under reduced pressure, to thereby yield a crude product. The crude product was isolated and purified through column chromatography (packing material: Silicagel 60 (product of Merck), eluent: methylene chloride/n-hexane), to thereby yield 0.84 g of the target product (pale yellow solid, yield: 60%). The structure of the obtained product was confirmed through $^1$H-NMR spectroscopy (solvent for measurement: CDCl$_3$) with reference to an integrated value at 6.74 ppm (2H) attributed to benzene ring proton Ha (see formula (11)) having two adjacent nitrogen atoms, from the fact that the ratio of the integrated value of the benzene-ring-originating protons to that of the thiophene-ring-originating protons coincides with that of the target structure product. Hereinafter, in descriptions in relation to other generations, Ha also refers to a benzene ring proton having two adjacent nitrogen atoms. The measurement data are shown below. The weight average molecular weight (Mw), number average molecular

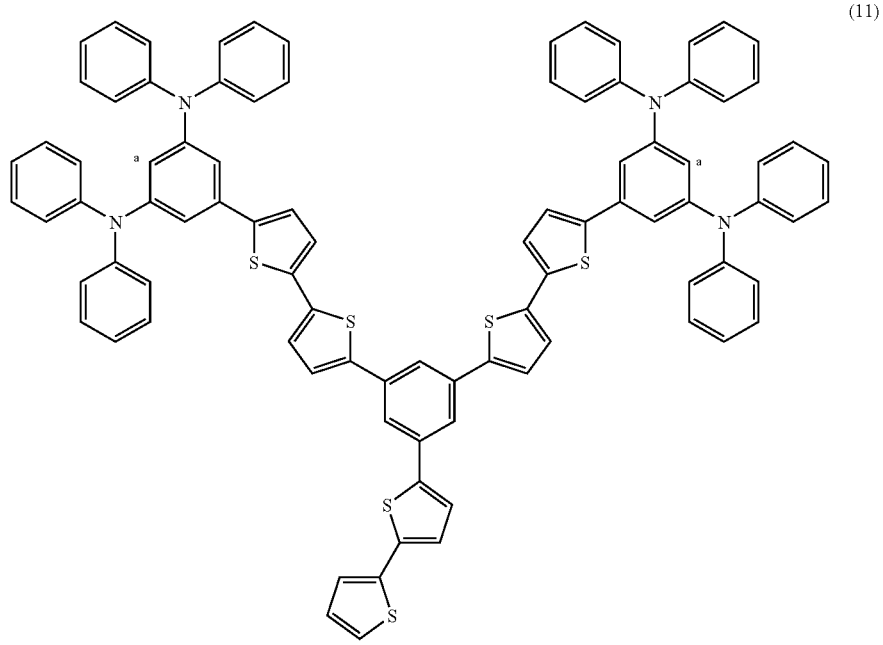

(11)

weight (Mn), and molecular weight distribution (Mw/Mn), as measured through GPC were found to be 1,265, 1,241, and 1.019, respectively. These values indicate that the target polymer has high purity and assumes a single dispersion state.

$^1$H NMR (CDCl$_3$) δ7.66 (d, J=1.2 Hz, benzene ring, 2H), δ7.65 (t, J=1.2 Hz, benzene ring, 1H), δ7.32 (d, J=3.6 Hz, thiophene ring, 1H), δ7.30 (d, J=3.6 Hz, thiophene ring, 2H), δ7.25-7.22 (m, benzene ring, 16H and thiophene ring, 2H), δ7.18 (d, J=3.6 Hz, thiophene ring, 1H), δ7.13-7.10 (m, benzene ring, 16H and thiophene ring, 2H), 7.08 (d, J=3.6 Hz, thiophene ring, 2H), 7.05 (dd, J=5.2 Hz, J=3.6 Hz, thiophene ring, 1H), 7.02-6.98 (m, benzene ring, 8H and thiophene ring, 2H), 6.92 (d, J=2.0 Hz, benzene ring, 4H), 6.74 (t, J=2.0 Hz, benzene ring, 2H).

Suzuki Coupling Reaction Involving Continuous/Intermittent Addition of Organic Boron Compound and Intermittent Addition of Base Catalyst>

In a nitrogen atmosphere, THF (4 mL) and water (1 mL) were added to a mixture of 5-(3,5-dibromophenyl)-2,2'-bithiophene (0.40 g) which had been produced in Synthesis Example 1-1; palladium acetate (13 mg); triphenylphosphine (46 mg); and sodium carbonate (0.11 g), and the resultant mixture was heated in an oil bath at 80° C. To the mixture, a solution of 5-(5'-boronic acid-[2,2']bithiophenyl-5-yl)-N,N,N',N'-tetraphenyl-1,3-phenylenediamine (0.65 g) obtained in Synthesis Example 1-3 dissolved in tetrahydrofuran (3 mL) was added dropwise over one hour, and the mixture was allowed to react under reflux conditions for 0.5 hours. Sodium carbonate (0.11 g) dissolved in water (1 mL) was added to the reaction mixture. Subsequently, a solution in tetrahydrofuran (3 mL) of 5-(5'-boronic acid-[2,2']bithiophenyl-5-yl)-N,N,N',N'-tetraphenyl-1,3-phenylenediamine (0.65 g) which had been prepared in Synthesis Example 1-3 was added dropwise over one hour to the resultant mixture, followed by allowing the mixture to react for 5.5 hours under reflux conditions.

After completion of reaction, the reaction mixture was cooled to room temperature, and water (20 mL) was added thereto. The resultant reaction mixture was subjected to extraction with methylene chloride, and the formed organic layer was washed with water. The organic layer was dried over sodium sulfate, and the solvent was distilled off under reduced pressure, to thereby yield a crude product. The crude product was subjected to isolation/purification through column chromatography (packing material: Silicagel 60 (product of Merck), eluent: methylene chloride/n-hexane), to thereby yield 1.14 g of the target product (pale yellow solid, yield: 82%). The yield was confirmed to be enhanced through continuous and intermittent addition. The structure of the obtained product was confirmed from the fact that the $^1$H-NMR spectrum coincides with that of the product through the aforementioned <Suzuki coupling not employing continuous/intermittent addition> and the fact that molecular weight values (obtained through GPC) of the target product almost coincide those of the aforementioned product.

SYNTHESIS EXAMPLE 1-5

Synthesis of 2nd-generation Dendrimer Represented by the Following Formula

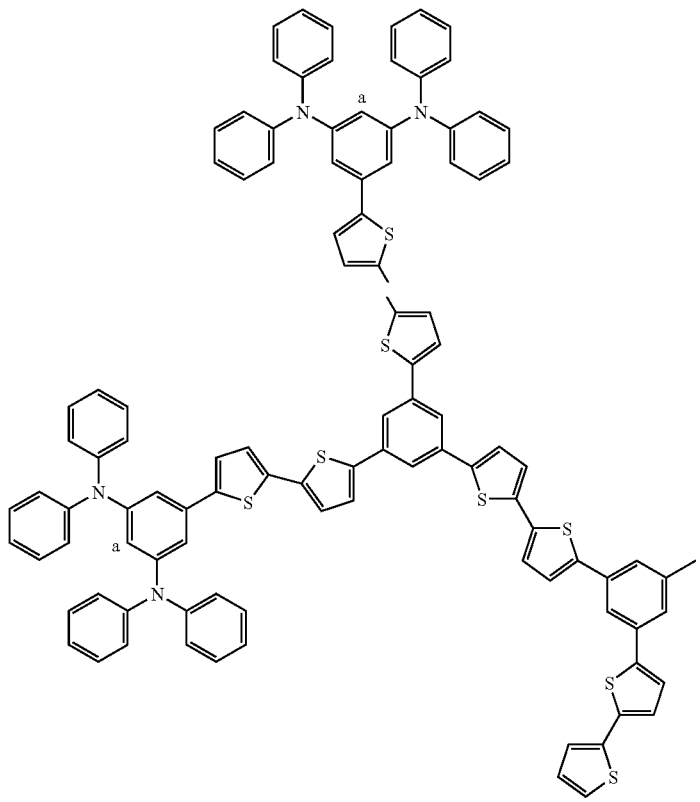

-continued

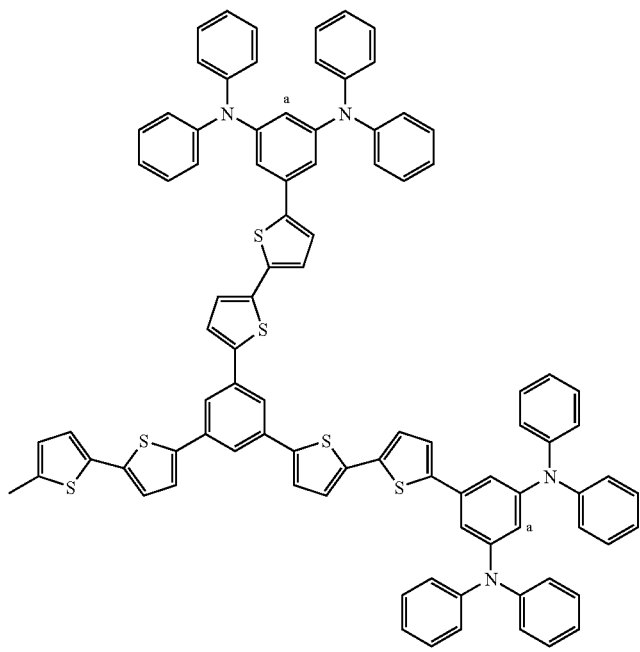

wherein, "a" represents the position of proton Ha, on which an integrated value obtained by $^1$H-NMR spectroscopy was evaluated.

<Synthesis of Boronic Acid Derivative of 1st-generation Dendrimer Represented by the Following Formula (12) Through Conversion, to Active Group $B(OH)_2$, of α-position Hydrogen of the Corresponding Thiophene Ring of 1st-generation Dendrimer>

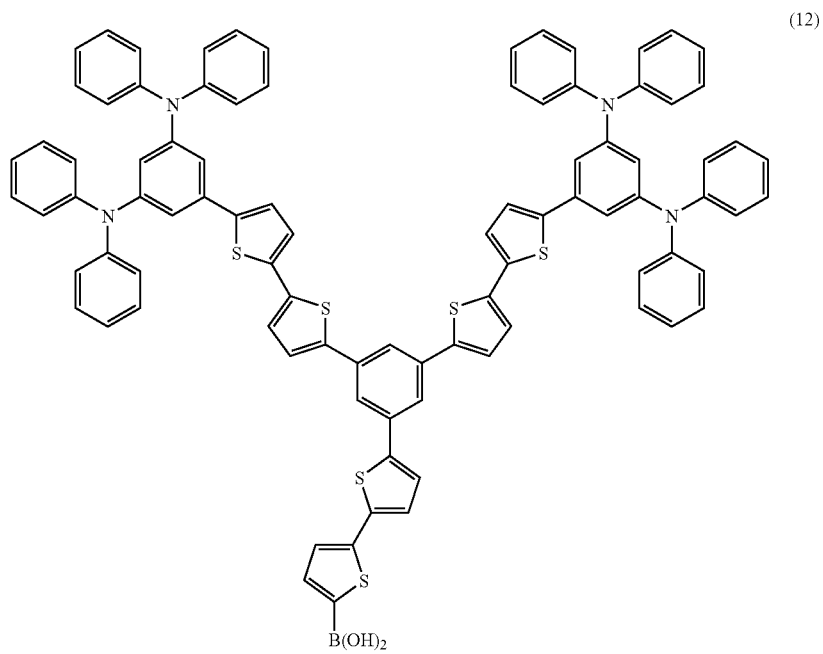

(12)

In a nitrogen atmosphere, the 1st-generation dendrimer (1.4 g) which had been produced in Synthesis Example 1-4 was dissolved in dehydrated tetrahydrofuran, and the solution was cooled in a dry ice-methanol bath. After cooling, a 10-wt. % lithium diisopropylamide/n-hexane suspension (2.1 g, product of Aldrich) was added dropwise thereto, and the mixture was allowed to react for one hour. Subsequently, trimethoxyborane (0.42 g) was added dropwise thereto, and the resultant mixture was allowed to react for one hour. After completion of reaction, water was added thereto for hydrolysis. Thereafter, the cooling bath was removed, whereby the temperature of the reaction mixture was elevated to room temperature. An aqueous saturated ammonium chloride solution and diethyl ether were added to the reaction mixture, and the resultant mixture was stirred and left to stand. The formed organic layer was isolated from the mixture, and the aqueous layer was subjected to extraction with a solvent mixture of tetrahydrofuran and diethyl ether (volume ratio: 1/2). The organic layer obtained through extraction was combined with the above organic layer, and the resultant mixture was washed with an aqueous saturated sodium chloride solution. The mixture was dried over sodium sulfate, and the solvent was distilled off under reduced pressure, to thereby yield a crude product. The crude product was recrystallized from tetrahydrofuran/n-hexane, to thereby yield 0.9 g of the target product; i.e., a 1st-generation boronic acid derivative (hereinafter abbreviated as "G1-B(OH)$_2$") (pale yellow solid, yield: 63%). The structure of the product was confirmed through $^1$H-NMR spectroscopy (solvent for measurement: DMSO-d$^6$) from the fact that a peak attributed to the OH proton of the boronic acid is observed at about 8.3 ppm and that the ratio of the integrated value of the benzene-ring-originating protons to that of the thiophene-ring-originating protons coincides with that of the target structure product.

<Suzuki Coupling Reaction not Employing Continuous/Intermittent Addition>

In a nitrogen atmosphere, THF (3 mL) and water (0.6 mL) were added to a mixture of G1-B(OH)$_2$ (0.9 g); 5-(3,5-dibromophenyl)-2,2'-bithiophene (0.12 g) which had been produced in Synthesis Example 1-1; palladium acetate (4 mg); triphenylphosphine (14 mg); and sodium carbonate (66 mg), and the resultant mixture was allowed to react for eight hours under reflux conditions. After completion of reaction, the reaction mixture was cooled to room temperature, and water (3 mL) was added thereto. The resultant mixture was subjected to extraction with methylene chloride, and the formed organic layer was washed with water. The organic layer was dried over sodium sulfate, and the solvent was distilled off under reduced pressure, to thereby yield a crude product. The crude product was isolated and purified through column chromatography (packing material: Silicagel 60 (product of Merck), eluent: methylene chloride/n-hexane), to thereby yield 0.47 g of the target product; i.e., a 2nd-generation dendrimer (pale yellow solid, yield: 52%). The structure of the obtained product was confirmed through $^1$H-NMR spectroscopy (solvent for measurement: CDCl$_3$) with reference to an integrated value at about 6.7 ppm (4H) attributed to benzene ring proton Ha having two adjacent nitrogen atoms, from the fact that the ratio of the integrated value of the benzene-ring-originating protons to that of the thiophene-ring-originating protons, observed at about 6.9 to about 7.4 ppm and about 7.6 to about 7.8 ppm, coincides with that of the target structure product. The weight average molecular weight (Mw), number average molecular weight (Mn), and molecular weight distribution (Mw/Mn), as measured through GPC were found to be 3,514, 3,385, and 1.038, respectively. These values indicate that the target polymer has high purity and assumes a single dispersion state.

<Suzuki Coupling Reaction Involving Continuous/Intermittent Addition of Organic Boron Compound and Intermittent Addition of Base Catalyst>

In a nitrogen atmosphere, THF (1.6 mL) and water (0.3 mL) were added to a mixture of 5-(3,5-dibromophenyl)-2,2'-bithiophene (0.12 g) which had been produced in Synthesis Example 1-1; palladium acetate (4 mg); triphenylphosphine (14 mg); and sodium carbonate (33 mg), and the resultant mixture was heated in an oil bath at 80° C. To the mixture, a solution of G1-B(OH)$_2$ (0.45 g) dissolved in tetrahydrofuran (0.7 mL) was added dropwise over one hour, and the mixture was allowed to react under reflux conditions for 0.5 hours. Sodium carbonate (33 mg) dissolved in water (0.3 mL) was added to the reaction mixture. Subsequently, another solution of G1-B(OH)$_2$ (0.45 g) dissolved in tetrahydrofuran (0.7 mL) was added dropwise over one hour to the resultant mixture, followed by allowing the mixture to react for 5.5 hours under reflux conditions.

After completion of reaction, the reaction mixture was cooled to room temperature, and water (3 mL) was added thereto. The resultant reaction mixture was subjected to extraction with methylene chloride, and the formed organic layer was washed with water. The organic layer was dried over sodium sulfate, and the solvent was distilled off under reduced pressure, to thereby yield a crude product. The crude product was subjected to isolation/purification through column chromatography (packing material: Silicagel 60 (product of Merck), eluent: methylene chloride/n-hexane), to thereby yield 0.64 g of the target product (a 2nd-generation dendrimer, pale yellow solid, yield: 71%). The yield was confirmed to be enhanced through continuous and intermittent addition. The structure of the obtained product was confirmed from the fact that the $^1$H-NMR spectrum coincides with that of the product through the aforementioned <Suzuki coupling not employing continuous/intermittent addition> and the fact that molecular weight values (obtained through GPC) of the target product almost coincide with those of the aforementioned product.

SYNTHESIS EXAMPLE 1-6
Synthesis of 3rd-generation Dendrimer Represented by the Following Formula (13)
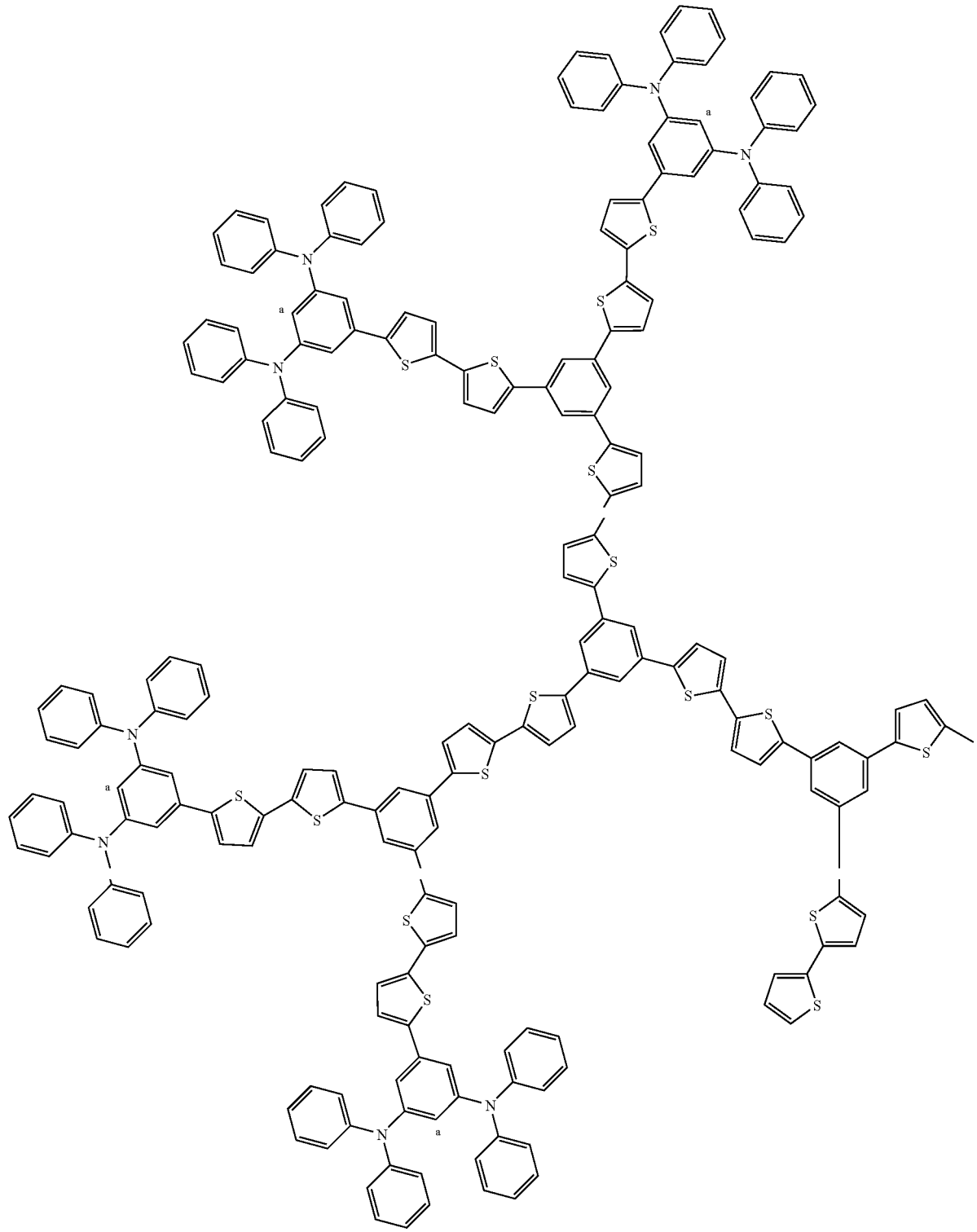
(13)

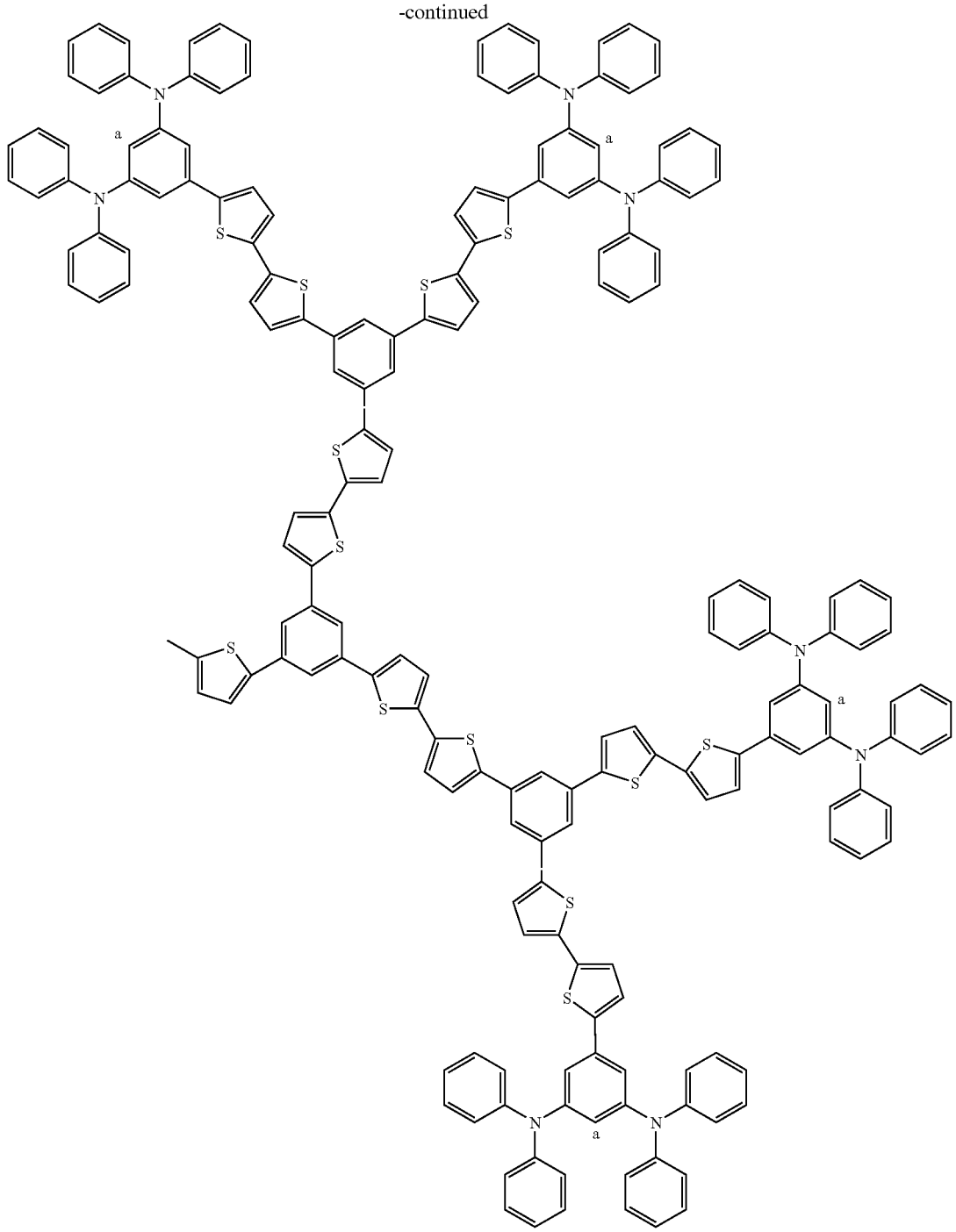

wherein, "a" represents the position of proton Ha, on which an integrated value obtained by $^1$H-NMR spectroscopy was evaluated.

A boronic acid derivative of the 2nd-generation dendrimer was synthesized through conversion, to active group B(OH)$_2$, of α-position hydrogen of the corresponding thiophene ring of the 2nd-generation dendrimer which had been synthesized in Synthesis Example 1-5. Subsequently, the derivative underwent Suzuki cross-coupling reaction with 5-(3,5-dibromophenyl)-2,2'-bithiophene which had been synthesized in Synthesis Example 1-1, to thereby yield a 3rd-generation dendrimer. In the above synthesis, the procedure of Synthesis Example 1-5 was repeated, except that the 2nd-generation dendrimer was employed instead of the 1st-generation dendrimer. The structure of the obtained product was confirmed through $^1$H-NMR spectroscopy (solvent for measurement: CDCl$_3$) with reference to an integrated value at about 6.7 ppm (8H) attributed to benzene ring proton Ha having two adjacent nitrogen atoms, from the fact that the ratio of the integrated value of the benzene-ring-originating protons to that of the thiophene-ring-originating protons, observed at about 6.9 to about 7.4 ppm and about 7.6 to about 7.8 ppm, coincides with that of the target structure product. The weight average molecular weight (Mw), number average molecular weight (Mn), and molecular weight distribution (Mw/Mn), as measured through GPC were found to be 7,890, 7,610, and 1.037, respectively. These values indicate that the target polymer has high purity and assumes a single dispersion state.

SYNTHESIS EXAMPLE 2

1st-generation, 3-branched Dendrimer Represented by the Following Formula (Bonding of 1st-generation Dendrimer to Benzene Core <Suzuki Coupling Reaction not Employing Continuous/Intermittent Addition>

In a nitrogen atmosphere, THF (6 mL) and water (1 mL) were added to a mixture of the boronic acid derivative of the 1st-generation dendrimer (i.e., G1-B(OH)$_2$) represented by formula (12) which had been produced through "conversion, to active group B(OH)$_2$ of α-position hydrogen of the corresponding thiophene ring of 1st-generation dendrimer" of Synthesis Example 1-5 (1.03 g); 1,3,5-tribromobenzene (68 mg); palladium acetate (15 mg); triphenylphosphine (51 mg); and sodium carbonate (95 mg), and the resultant mixture was allowed to react for eight hours under reflux conditions. After completion of reaction, the temperature of the reaction mixture was lowered to room temperature, and water (3 mL) was added thereto. The resultant mixture was subjected to extraction with chloroform, and the formed organic layer was

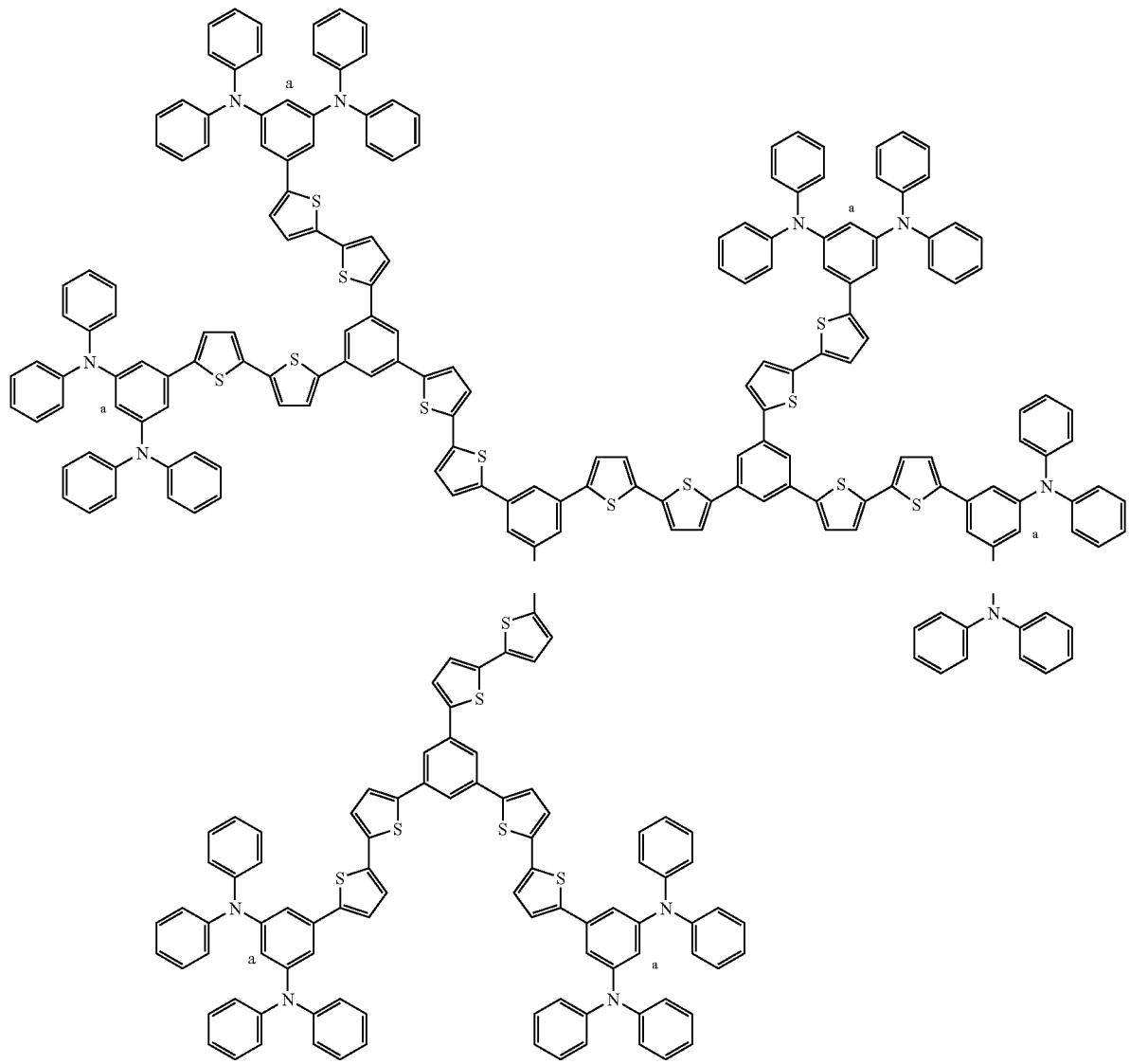

wherein, "a" represents the position of proton Ha, on which an integrated value obtained by $^1$H-NMR spectroscopy was evaluated.

washed with water. The organic layer was dried over sodium sulfate, and the solvent was distilled off under reduced pressure, to thereby yield a crude product. The crude product was isolated and purified through column chromatography (packing material: Silicagel 60 (product of Merck), eluent: methylene chloride/n-hexane) and subsequently recrystallized from chloroform, to thereby yield 0.36 g of the target product; i.e., a 1st-generation, 3-branched dendrimer (pale yellow solid, yield: 39%). The structure of the obtained product was confirmed through $^1$H-NMR spectroscopy (solvent for measurement: CDCl$_3$) with reference to an integrated value at about 6.7 ppm (6H) attributed to benzene ring proton Ha having two adjacent nitrogen atoms, from the fact that the ratio of the integrated value of the benzene-ring-originating protons to that of the thiophene-ring-originating protons, observed at about 6.9 to about 7.2 ppm and about 7.4 to about 7.5 ppm, coincides with that of the target structure product. The measurement data are shown below. The weight average molecular weight (Mw), number average molecular weight (Mn), and molecular weight distribution (Mw/Mn), as measured through GPC were found to be 5,017, 4,667, and 1.073, respectively. These values indicate that the target polymer has high purity and assumes a single dispersion state.

$^1$H NMR (CDCl$_3$) 7.48 (s, benzene ring, 3H), 7.46 (s, benzene ring, 6H), 7.43 (s, benzene ring, 3H), 7.22-7.18 (m, benzene ring and thiophene ring, 57H), 7.10-7.08 (m, benzene ring and thiophene ring, 60H), 6.99-6.94 (m, benzene ring and thiophene ring, 33H), 6.90 (d, J=0.8 Hz, benzene ring, 12H), 6.87 (d, J=3.2 Hz, thiophene ring, 6H), 6.73 (t, J=2.0 Hz, benzene ring, 6H).

<Suzuki Coupling Reaction Involving Continuous/Intermittent Addition of Organic Boron Compound and Intermittent Addition of Base Catalyst>

In a nitrogen atmosphere, THF (1.5 mL) and water (0.4 mL) were added to a mixture of 1,3,5-tribromobenzene (68 mg); palladium acetate (15 mg); triphenylphosphine (51 mg); and sodium carbonate (32 mg), and the resultant mixture was heated in an oil bath at 80° C. To the mixture, a solution of the 1st-generation dendrimer boronic acid derivative G1-B(OH)$_2$ (0.34 g)—which had been produced in Synthesis Example (1-5) through conversion; i.e., conversion, to active group B(OH)$_2$, of α-position hydrogen of the corresponding thiophene ring of 1st-generation dendrimer, and which is represented by formula (12)—dissolved in tetrahydrofuran (1.5 mL) was added dropwise over one hour, and the mixture was allowed to react under reflux conditions for 0.5 hours. Sodium carbonate (32 mg) dissolved in water (0.3 mL) was added to the reaction mixture. Subsequently, a solution of G1-B(OH)$_2$ (0.34 g) dissolved in tetrahydrofuran (1.5 mL) was added dropwise for one hour to the resultant mixture, followed by allowing the mixture to react for 0.5 hours under reflux conditions. Sodium carbonate (32 mg) dissolved in water (0.3 mL) was added to the reaction mixture. Subsequently, a solution of G1-B(OH)$_2$ (0.34 g) dissolved in tetrahydrofuran (1.5 mL) was added dropwise for one hour to the resultant mixture, followed by allowing the mixture to react for four hours under reflux conditions. After completion of reaction, the reaction mixture was cooled to room temperature, and water (3 mL) was added thereto. The resultant reaction mixture was subjected to extraction with chloroform, and the formed organic layer was washed with water. The organic layer was dried over sodium sulfate, and the solvent was distilled off under reduced pressure, to thereby yield a crude product. The crude product was subjected to isolation/purification through column chromatography (packing material: Silicagel 60 (product of Merck), eluent: methylene chloride/n-hexane), and then recrystallized from chloroform, to thereby yield 0.48 g of the target product (a 1st-generation, 3-branched dendrimer, pale yellow solid, yield: 52%). The yield was confirmed to be enhanced through continuous and intermittent addition. The structure of the obtained product was confirmed from the fact that the $^1$H-NMR spectrum coincides with that of the product through the aforementioned <Suzuki coupling not employing continuous/intermittent addition> and the fact that molecular weight values (obtained through GPC) of the target product almost coincide those of the aforementioned product.

SYNTHESIS EXAMPLE 3

Synthesis of 1st-generation, 3-Branched Dendrimer

SYNTHESIS EXAMPLE 3-1

Synthesis of 3,5-bis[2-(5-bromothienyl)]-2-thienylbenzene and 1,3,5-tris[2-(5-bromothienyl)]benzene, Which Serve as Monomer unit compounds (c) Forming a Dendritic Structure and are Represented by the Following formula:

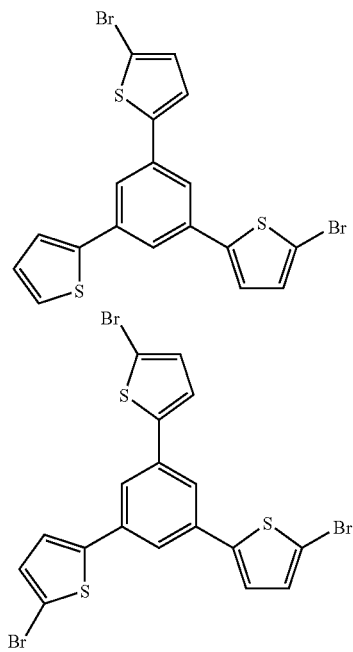

<Suzuki Cross-coupling Reaction not Employing Continuous Addition of Organic Boron Compound>

In a nitrogen atmosphere, thiophene (14 g) was dissolved in dehydrated tetrahydrofuran (100 mL), and the solution was cooled in a dry ice-methanol bath. After cooling of the solution to −70° C. or lower, a 1.6M n-butyllithium/hexane solution (100 mL) was added dropwise to the cooled solution over 40 minutes. The mixture was allowed to react for one hour, and trimethoxyborane (20 g) was added dropwise to the reaction mixture over 10 minutes. The cooling bath was removed, and the mixture was gradually heated to room temperature, thereby producing reaction mixture A. 1,3,5-Tribromobenzene (13 g), palladium acetate (0.8 g), triphenylphosphine (2.9 g), sodium carbonate (8.7 g), methanol (130 mL) and water (25 mL) which had been degassed and nitrogen-substituted in advance, were added to reaction mixture A, and the mixture was further nitrogen-substituted. The resultant mixture was allowed to react in an oil bath at 85° C. for four hours. After completion of reaction, methanol (50 mL) and water (100 mL) were added to the reaction mixture, followed by cooling to room temperature. The formed precipitates were removed through filtration, and methylene chloride (100 mL) and water (100 mL) were added to the filtrate. The insoluble component contained in the filtrate was removed through filtration, and the organic layer was separated. The organic layer was washed sequentially with water and an aqueous sodium chloride saturated solution and dried over sodium sulfate, and the solvent was distilled off under reduced pressure, to thereby yield a crude product. The crude product was purified through column chromatography (packing material: Silicagel 60 (product of Merck), eluent: methylene chloride/n-hexane) and subsequently recrystallized from methylene chloride-methanol, to thereby yield 7.6 g of 1,3,5-tris(2-thienyl)benzene (yield 57%, white powder) serving as an intermediate and represented by the following formula (13). The structure was confirmed from a $^1$H-NMR spectrum. The measurement data are shown below.

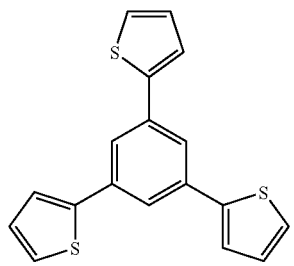

(13)

$^1$H NMR (CDCl$_3$) δ 7.81 (s, benzene ring, 3H), δ 7.74 (dd, J=3.6, 0.8 Hz, thiophene ring, 3H), δ 7.65 (dd, J=5.2, 0.8 Hz, thiophene ring, 3H), δ 7.21 (dd, J=5.2, 3.6 Hz, thiophene ring, 3H).

<Suzuki Coupling Involving Continuous Addition of Organic Boron Compound>

In a nitrogen atmosphere, thiophene (14 g) was dissolved in dehydrated tetrahydrofuran (100 mL), and the solution was cooled in a dry ice-methanol bath. After cooling of the solution to −70° C. or lower, a 1.6M n-butyllithium/hexane solution (100 mL) was added dropwise to the cooled solution over 40 minutes. The mixture was allowed to react for one hour, and trimethoxyborane (20 g) was added dropwise to the reaction mixture over 10 minutes. The cooling bath was removed, and the mixture was gradually heated to room temperature, thereby producing reaction mixture A. 1,3,5-Tribromobenzene (13 g), palladium acetate (0.8 g), triphenylphosphine (2.9 g), and sodium carbonate (8.7 g) were added to methanol (130 mL) and water (25 mL) which had been degassed and nitrogen-substituted in advance, and the mixture was further nitrogen-substituted. The reaction mixture A prepared in advance was added dropwise to the mixture over 80 minutes under stirring in an oil bath at 85° C., and the resultant mixture was allowed to react for another three hours. After completion of reaction, methanol (50 mL) and water (100 mL) were added the reaction mixture, followed by cooling to room temperature. The formed precipitates were removed through filtration, and methylene chloride (100 mL) and water (100 mL) were added to the filtrate. The insoluble component contained in the filtrate was removed through filtration, and the organic layer was separated. The organic layer was washed sequentially with water and an aqueous sodium chloride saturated solution and dried over sodium sulfate, and the solvent was distilled off under reduced pressure, to thereby yield a crude product. The crude product was subjected to isolation through column chromatography (packing material: Silicagel 60 (product of Merck), eluent: methylene chloride/n-hexane) and subsequently recrystallized from methylene chloride-methanol, to thereby yield 12 g of 1,3,5-tris(2-thienyl)benzene (yield 90%, white powder) serving as an intermediate and represented by the following formula (13). The yield was confirmed to be enhanced through continuous addition of organic boron compound. The structure of the obtained product was confirmed from the fact that the $^1$H-NMR spectrum coincides with that of the product through the aforementioned <Suzuki cross-coupling reaction not employing continuous addition of organic boron compound>.

<Bromination of Intermediate 1,3,5-tris(2-thienyl)benzene>

The thus-obtained 1,3,5-tris(2-thienyl)benzene (2.0 g) was dissolved in dimethylformamide (10 mL), and the solution was cooled in an ice-water bath. A solution of N-bromosuccinimide (2.4 g) in dimethylformamide (9 mL) was added to the cooled solution, and the cooling bath was removed. The mixture was heated to room temperature. After completion of reaction, water was added thereto. The resultant reaction mixture was subjected to extraction with chloroform, and the formed organic layer was washed with water. The organic layer was dried over sodium sulfate, and the solvent was distilled off under reduced pressure, to thereby yield a crude product. The crude product was subjected to isolation/purification through column chromatography (packing material: Silicagel 60 (product of Merck), eluent: chloroform/n-hexane), to thereby yield the target products; i.e., 1.05 g of 3,5-bis[2-(5-bromothienyl]-2-thienylbenzene (white solid) and 1.49 g of 1,3,5-tris[2-(5-bromothienyl)]benzene (white solid). The structures were confirmed from H-NMR spectra. The measurement data are shown below.

3,5-bis[2-(5-Bromothienyl)]-2-thienylbenzene
$^1$H NMR (CDCl$_3$) δ 7.64 (d, J=1.6 Hz, benzene ring, 2H) δ 7.52 (t, J=1.6 Hz, benzene ring, 1H), δ 7.39 (dd, J=1.2 Hz, J=3.6 Hz, thiophene ring, 1H), δ 7.35 (dd, J=1.2 Hz, J=5.2 Hz, thiophene ring, 1H), δ 7.15-7.12 (m, thiophene ring, 3H), δ 7.08 (d, J=4.0 Hz, thiophene ring, 2H). 1,3,5-tris[2-(5-Bromothienyl)benzene
$^1$H NMR (CDCl$_3$) δ 7.53 (s, benzene ring, 3H), δ 7.07 (d, J=4.0 Hz, thiophene ring, 3H), δ 7.00 (d, J=4.0 Hz, thiophene ring, 3H).

SYNTHESIS EXAMPLE 3-2

Synthesis of 1,3-dichloro-5-(2-thienyl)Benzene Represented by the Following Formula

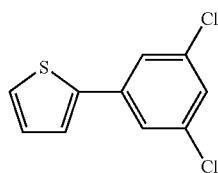

<Suzuki Cross-coupling not Employing Continuous Addition of Organic Boron Compound>

In a nitrogen atmosphere, thiophene (7.0 g) was dissolved in dehydrated tetrahydrofuran (55 mL), and the solution was cooled in a dry ice-methanol bath. After cooling of the solution to −70° C. or lower, a 1.6M n-butyllithium/hexane solution (50 mL) was added dropwise to the cooled solution over one hour. The mixture was allowed to react for one hour, and trimethoxyborane (9.8 g) was added dropwise to the reaction mixture over 10 minutes. The cooling bath was removed, and the mixture was gradually heated to room temperature, thereby producing reaction mixture A. Under nitrogen, 1-bromo-3,5-dichlorobenzene (16.3 g), palladium acetate (0.5 g), triphenylphosphine (1.7 g), sodium carbonate (6.9 g), methanol (150 mL) and water (30 mL) which had been degassed and nitrogen-substituted in advance, were added to reaction mixture A, and the mixture was further nitrogen-substituted. The resultant mixture was allowed to react in an oil bath at 85° C. for four hours. After completion of reaction, methanol (50 mL) and water (100 mL) were added the reaction mixture, followed by cooling to room temperature. The formed precipitates were removed through filtration, and methylene chloride (100 mL) and water (100 mL) were added to the filtrate. The insoluble component contained in the filtrate was removed through filtration, and the organic layer was separated. The organic layer was washed sequentially with water and an aqueous sodium chloride saturated solution (three times) and dried over sodium sulfate, and the solvent was distilled off under reduced pressure, to thereby yield a crude product. The crude product was purified through column chromatography (packing material: Silicagel 60 (product of Merck), eluent: methylene chloride/n-hexane), to thereby yield 11.7 g of the target product (yield 70%, white powder). The structure was confirmed from a $^1$H-NMR spectrum. The measurement data are shown below.

$^1$H NMR (CDCl$_3$) δ 7.47 (d, J=0.8 Hz, benzene ring, 2H) δ 7.35 (d, J=5.2 Hz, thiophene ring, 1H), δ 7.32 (d, J=3.6, thiophene ring, 1H), δ 7.26 (br, benzene ring, 1H), δ 7.09 (dd, J=5.2, 3.6 Hz, thiophene ring, 1H).

<Suzuki Cross-coupling Involving Continuous Addition of Organic Boron Compound>

Under nitrogen, 1-bromo-3,5-dichlorobenzene (16.3 g), palladium acetate (0.5 g), triphenylphosphine (1.7 g), and sodium carbonate (6.9 g) were added to methanol (150 mL) and water (30 mL) which had been degassed and nitrogen-substituted in advance, and the mixture was further nitrogen-substituted. The mixture was stirred in an oil bath at 85° C. The reaction mixture A which had been prepared in a manner similar to that of the above-mentioned <Suzuki cross-coupling reaction not employing continuous addition of organic boron compound> was added dropwise to the mixture over one hour, and the resultant mixture was allowed to react for further three hours. After completion of reaction, methanol (50 mL) and water (100 mL) were added the reaction mixture, followed by cooling to room temperature. The formed precipitates were removed through filtration, and methylene chloride (100 mL) and water (100 mL) were added to the filtrate. The insoluble component contained in the filtrate was removed through filtration, and the organic layer was separated. The organic layer was washed sequentially with water and an aqueous sodium chloride saturated solution (three times) and dried over sodium sulfate, and the solvent was distilled off under reduced pressure, to thereby yield a crude product. The crude product was purified through column chromatography (packing material: Silicagel 60 (product of Merck), eluent: methylene chloride/n-hexane), to thereby yield 15 g of the target product (yield 90%, white powder). The yield was confirmed to be enhanced as compared with the case of the above-mentioned <Suzuki cross-coupling not employing continuous addition of organic boron compound>. The structure of the obtained product was confirmed from the fact that the $^1$H-NMR spectrum coincides with that of the product obtained through the aforementioned <Suzuki cross-coupling reaction not employing continuous addition of organic boron compound>.

SYNTHESIS EXAMPLE 3-3

Synthesis of a Compound (a), 5-(2-thienyl)-N,N,N', N'-tetraphenyl-1,3-phenylenediamine, Represented by the Following Formula, Forming end Moieties of the Dendritic Structure

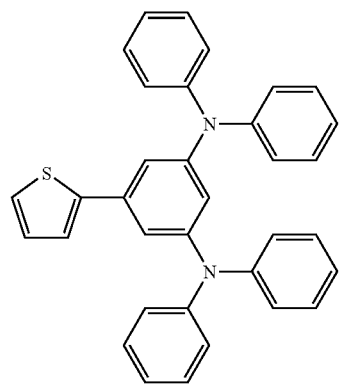

In a nitrogen atmosphere, tri-t-butylphosphine (35 mg) was added to a solution of palladium acetate (0.01 g) in xylene (50 mL), and the mixture was stirred for 10 minutes in an oil bath at 80° C., followed by cooling the mixture to room temperature, to thereby prepare a catalyst. Subsequently, in a nitrogen atmosphere, 1,3-dichloro-5-(2-thienyl)benzene (10 g) synthesized in Synthesis Example 3-2, diphenylamine (16 g), and potassium t-butoxide (12 g) were added to xylene (18 mL), and the mixture was heated in an oil bath at 80° C. The catalyst prepared above was added thereto, and the resultant mixture was allowed to react for 18 hours in the oil bath at 120° C. After completion of reaction, the reaction mixture was cooled to room temperature. The formed organic layer was washed with water, and the aqueous layer was subjected to extraction twice with methylene chloride. The organic layers were combined together and then washed with water. The resultant organic layer was dried over sodium sulfate, and the solvent was distilled off under reduced pressure, to thereby yield a crude product. The crude product was purified through column chromatography (packing material: Silicagel 60 (product of Merck), eluent: methylene chloride/n-hexane) and subsequently recrystallized from methylene chloride-methanol, to thereby yield 15 g of the target product (yield 70%, white powder). The structure was confirmed from a H-NMR spectrum. The measurement data are shown below.

$^1$H NMR (CDCl$_3$) δ 7.22 (t, benzene ring, J=7.6 Hz, 8H) δ 7.16 (dd, J=1.0, 5.2 Hz, thiophene ring, 1H), δ 7.09 (d, J=7.6 Hz, benzene ring, 8H), δ 7.06 (dd, J=1.0, 3.6 Hz, thiophene ring, 1H), δ 7.00-6.94 (m, benzene ring and thiophene ring, 5H), δ 6.91 (d, J=2.0 Hz, benzene ring, 2H), δ 6.73 (t, J=2.0 Hz, benzene ring, 1H).

$^1$H NMR (DMSO) δ 7.43 (dd, J=1.2, 5.2 Hz, thiophene ring, 1H) δ 7.29 (t, J=8.0 Hz, benzene ring, 8H), δ 7.43 (dd, J=1.2, 3.6 Hz, benzene ring, 1H), δ 7.07-7.00 (m, benzene ring and thiophene ring, 13H), δ 6.73 (d, J=2.0 Hz, benzene ring, 2H), δ 6.53 (t, J=2.0 Hz, benzene ring, 1H).

SYNTHESIS EXAMPLE 3-4

Synthesis of a Compound (b), 5-(5-boronic acid-thiophen-2-yl)-N,N,N',N'-tetraphenyl-1,3-phenylenediamine Represented by the Following Formula, Through Conversion, to Active Group B(OH)$_2$, of α-position Hydrogen of the Corresponding Thiophene Ring of Compound (a) Forming the End Moieties of the Dendritic Structure

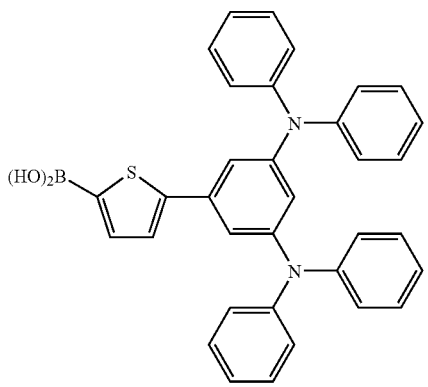

In a nitrogen atmosphere, diisopropylamine (3.2 g) was dissolved in dehydrated tetrahydrofuran (50 mL), and the solution was cooled in a dry ice-methanol bath. At a temperature of −70° C. or lower, a 1.6M n-butyllithium/hexane solution (19 mL) was added dropwise to the cooled solution over 10 minutes. The reaction mixture was allowed to react for 30 minutes at 0° C., to thereby prepare a lithium diisopropylamide (LDA) solution. Subsequently, 5-(2-thienyl)-N,N,N',N'-tetraphenyl-1,3-phenylenediamine (5.0 g) synthesized in Synthesis Example 3-3 was dissolved in dehydrated tetrahydrofuran (30 mL), and the solution was cooled in a dry ice-methanol bath. The LDA solution prepared above was added dropwise to the cooled solution over one hour. The resultant mixture was allowed to react for one hour at a temperature of −70° C. or lower, and trimethoxyborane (6.9 g) was added dropwise to the reaction mixture over 10 minutes. The mixture was gradually heated to room temperature over one hour. After completion of reaction, the reaction mixture was cooled in an ice-water bath, and diethyl ether (70 mL) and water (20 mL) were added thereto for hydrolysis, and the reaction mixture was heated to room temperature. Thereafter, water (50 mL) and an aqueous saturated ammonium chloride solution (70 mL) were added thereto, to thereby separate the organic layer. The organic layer was washed twice with an aqueous saturated ammonium chloride solution (120 mL) and twice with an aqueous saturated sodium chloride solution (120 mL), and dried over sodium sulfate. The solvent was distilled off under reduced pressure, to thereby yield 5.4 g of the target product (yield 99%, faintly yellow powder). The structure was confirmed from a $^1$H-NMR spectrum. The measurement data are shown below.

$^1$H NMR (DMSO) δ 8.20 (s, boronic acid, 2H), δ 7.52 (d, J=3.6 Hz, thiophene ring, 1H), δ 7.29 (t, J=3.6 Hz, benzene ring, 9H), δ 7.16 (d, J=3.6 Hz, thiophene ring, 1H), δ 7.07-7.02 (m, benzene ring, 12H), δ 6.75 (d, J=2.0 Hz, benzene ring, 1H), δ 6.54 (t, J=2.0 Hz, benzene ring 1H).

SYNTHESIS EXAMPLE 3-5

Synthesis of 1st-generation Dendron Represented by the Following Formula

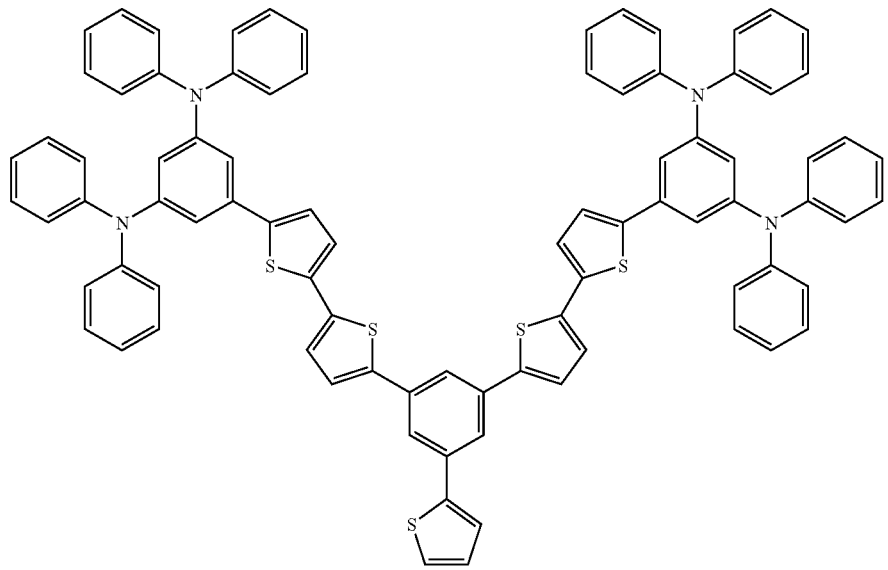

<Suzuki Cross-coupling Reaction not Employing Continuous/Intermittent Addition of Organic Boron Compound nor Intermittent Addition of Base Catalyst>

In a nitrogen atmosphere, THF (30 mL) and water (6 mL) were added to a mixture of 3,5-bis[2-(5-bromothienyl)]-2-thienylbenzene (1.49 g) which had been produced in Synthesis Example 3-1; 5-(5-boronic acid-thiophen-2-yl)-N,N,N', N'-tetraphenyl-1,3-phenylenediamine (3.98 g) which had been produced in Synthesis Example 3-4; palladium acetate (69 mg); triphenylphosphine (0.24 g); and sodium carbonate (0.85 g), and the resultant mixture was allowed to react for eight hours under reflux conditions. After completion of reaction, the reaction mixture was cooled to room temperature, and water (20 mL) was added thereto. The resultant reaction mixture was subjected to extraction with methylene chloride, and the formed organic layer was washed with water. The organic layer was dried over sodium sulfate, and the solvent was distilled off under reduced pressure, to thereby yield a crude product. The crude product was subjected to isolation/purification through column chromatography (packing material: Silicagel 60 (product of Merck), eluent: methylene chloride/n-hexane), to thereby yield 2.43 g of the target product (white solid, yield: 60%). The structure was confirmed from a $^1$H-NMR spectrum. The measurement data are shown below.

$^1$H NMR (CDCl$_3$) δ 7.68 (d, J=1.6 Hz, benzene ring, 2H) δ 7.65 (t, J=1.6 Hz, benzene ring, 1H), δ 7.40 (dd, J=1.0 Hz, J=3.4 Hz, thiophene ring, 1H), δ 7.34 (dd, J=1.0 Hz, J=5.2 Hz, thiophene ring, 1H), δ 7.29 (d, J=3.6 Hz, thiophene ring, 2H), δ 7.26-7.22 (m, benzene ring, 16H and thiophene ring, 2H), δ 7.13-7.08 (m, benzene ring, 16H and thiophene ring, 4H), 7.02-6.98 (m, benzene ring, 8H and thiophene ring, 1H), 6.91 (d, J=2.0 Hz, benzene ring, 4H), 6.74 (t, J=2.0 Hz, benzene ring, 2H).

<Suzuki Cross-coupling Reaction Involving Continuous/Intermittent Addition of Organic Boron Compound and Intermittent Addition of Base Catalyst>

In a nitrogen atmosphere, THF (10 mL) and water (3 mL) were added to a mixture of 3,5-bis[2-(5-bromothienyl)]-2-thienylbenzene (1.49 g) which had been produced in Synthesis Example 3-1; palladium acetate (69 mg); triphenylphosphine (0.24 g); and sodium carbonate (0.43 g), and the resultant mixture was heated in an oil bath at 80° C. To the mixture, a solution of 5-(5-boronic acid-thiophen-2-yl)-N,N,N',N'-tetraphenyl-1,3-phenylenediamine (produced in Synthesis Example 3-4, 1.99 g) dissolved in tetrahydrofuran (10 mL) was added dropwise over one hour, and the mixture was allowed to react under reflux conditions for 0.5 hours. Sodium carbonate (0.42 g) dissolved in water (3 mL) was added to the reaction mixture. Subsequently, a solution in tetrahydrofuran (10 mL) of 5-(5-boronic acid-thiophen-2-yl)-N,N,N',N'-tetraphenyl-1,3-phenylenediamine (1.99 g) prepared in Synthesis Example 3-4 was added dropwise over one hour to the resultant mixture, followed by allowing the mixture to react for 5.5 hours under reflux conditions.

After completion of reaction, the reaction mixture was cooled to room temperature, and water (20 mL) was added thereto. The resultant reaction mixture was subjected to extraction with methylene chloride, and the formed organic layer was washed with water. The organic layer was dried over sodium sulfate, and the solvent was distilled off under reduced pressure, to thereby yield a crude product. The crude product was subjected to isolation/purification through column chromatography (packing material: Silicagel 60 (product of Merck), eluent: methylene chloride/n-hexane), to thereby yield 3.40 g of the target product (white solid, yield: 84%). The yield was confirmed to be enhanced through continuous/intermittent addition of organic boron compound and intermittent addition of base catalyst. The structure was confirmed from the fact that the $^1$H-NMR spectrum of the compound coincides with that of the compound produced in Synthesis Example 3-5.

SYNTHESIS EXAMPLE 3-6

Synthesis of 1st-generation, 3-branched Dendrimer Having the Same Structure as the Dendrimer Produced in Synthesis Example 2

<Synthesis of 1st-generation Dendrimer Boronic Acid Derivative Represented by the Following Formula (14), Through Conversion, to Active Group B(OH)$_2$, of α-position Hydrogen of the Corresponding Thiophene Ring of 1st-generation Dendrimer:

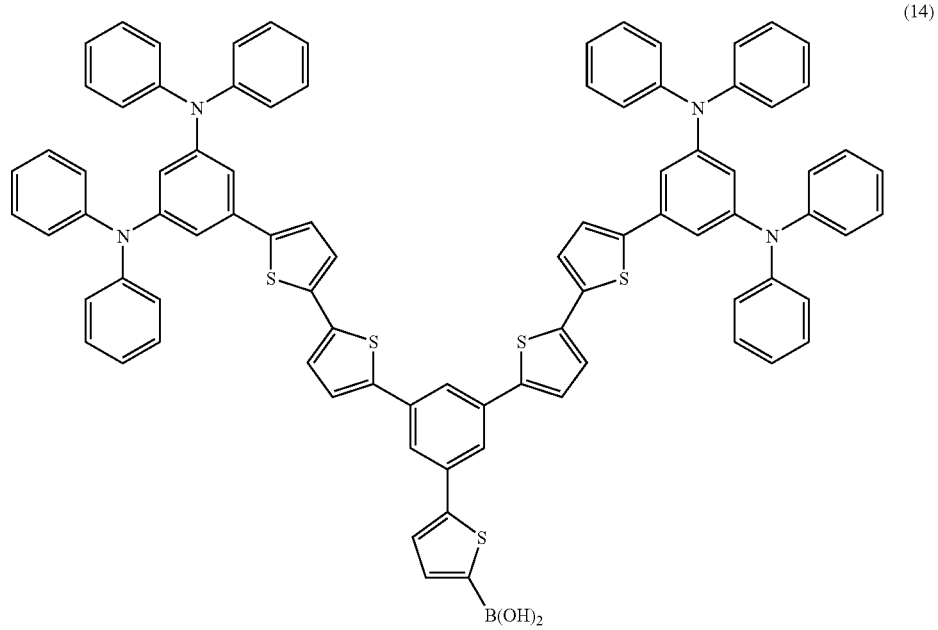

(14)

In a nitrogen atmosphere, diisopropylamine (0.73 g) was dissolved in dehydrated tetrahydrofuran (10 mL), and the solution was cooled in a dry ice-methanol bath. At a temperature of −70° C. or lower, a 1.6M n-butyllithium/hexane solution (4.3 mL) was added dropwise to the cooled solution over 10 minutes. The reaction mixture was allowed to react for 15 minutes at 0° C., to thereby prepare a lithium diisopropylamide (LDA) solution. Subsequently, the 1st-generation dendrimer (2.0 g) prepared in Synthesis Example 3-5 was dissolved in dehydrated tetrahydrofuran (30 mL), and the solution was cooled in a dry ice-methanol bath. The LDA solution prepared above was added dropwise to the cooled solution over 20 minutes. The resultant mixture was allowed to react for one hour at a temperature of −70° C. or lower, and trimethoxyborane (1.6 g) was added dropwise to the reaction mixture over 10 minutes. The mixture was gradually heated to room temperature over one hour. After completion of reaction, the reaction mixture was cooled in an ice-water bath, and diethyl ether (20 mL) and water (20 mL) were added thereto for hydrolysis. The reaction mixture was recovered to room temperature. Thereafter, an aqueous saturated ammonium chloride solution (20 mL) was added thereto, to thereby separate the organic layer. The organic layer was washed three times with an aqueous saturated ammonium chloride solution (50 mL) and twice with an aqueous saturated sodium chloride solution (50 mL), and dried over sodium sulfate. The solvent was distilled off under reduced pressure, to thereby yield a crude product. The crude product was recrystallized from tetrahydrofuran/n-hexane, to thereby 2.0 g of the target product, a 1st-generation dendrimer boronic acid derivative, (yield 97%, pale yellow solid). The structure of the product was confirmed through $^1$H-NMR spectroscopy (solvent for measurement: DMSO-$d^6$) from the fact that a peak attributed to the OH proton of the boronic acid is observed at about 8.3 ppm and the fact that the ratio of the integrated value of the benzene-ring-originating protons to that of the thiophene-ring-originating protons coincides with that of the target structure product.

<Suzuki Cross-coupling not Employing Continuous/Intermittent Addition of Organic Boron Compound nor Intermittent Addition of Base Catalyst>

In a nitrogen atmosphere, THF (28 mL) and water (2 mL) were added to a mixture of the 1st-generation dendrimer boronic acid derivative (2.1 g) represented by formula (14) above; 1,3,5-tris[2-(5-bromothienyl)]benzene (238 mg) which had been produced in Synthesis Example 3-1; palladium acetate (14 mg); triphenylphosphine (50 mg); and sodium carbonate (0.18 g), and the resultant mixture was allowed to react for eight hours under reflux conditions. After completion of reaction, the reaction mixture was cooled to room temperature, and water (20 mL) was added thereto. The resultant reaction mixture was subjected to extraction with chloroform, and the formed organic layer was washed with water. The organic layer was dried over sodium sulfate, and the solvent was distilled off under reduced pressure, to thereby yield a crude product. The crude product was subjected to isolation/purification through column chromatography (packing material: Silicagel 60 (product of Merck), eluent: methylene chloride/n-hexane) and then recrystallized from chloroform, to thereby yield 0.74 g of the target product, a 1st-generation, 3-branched dendrimer, (pale yellow solid, yield: 41%). The structure of the obtained product was confirmed from the fact that the $^1$H-NMR spectrum coincides with that of the product of Synthesis Example 2. The molecular-weight-related measurements obtained through GPC were as follows: weight average molecular weight (Mw) of 5,240, number average molecular weight (Mn) of 4,855, and molecular weight distribution factor (Mw/Mn) of 1.079. These values indicate that the target polymer has high purity and assumes a single dispersion state.

<Suzuki Cross-coupling Involving Continuous/Intermittent Addition of Organic Boron Compound and Intermittent Addition of Base Catalyst>

In a nitrogen atmosphere, THF (2 mL) and water (0.4 mL) were added to a mixture of 1,3,5-tris[2-(5-bromothienyl)] benzene (238 mg) which had been produced in Synthesis Example 3-1; palladium acetate (14 mg); triphenylphosphine (50 mg); and sodium carbonate (0.06 g), and the resultant mixture was heated at 80° C. in an oil bath. To the resultant mixture, a solution of the 1st-generation dendrimer boronic acid derivative (0.7 g) represented by formula (14) dissolved in tetrahydrofuran (8.4 mL) was added dropwise over one hour, and the mixture was allowed to react under reflux conditions for 0.5 hours. Sodium carbonate (0.06 g) dissolved in water (0.4 mL) was added to the reaction mixture. To the resultant mixture, a solution of the 1st-generation dendrimer boronic acid derivative (0.7 g) represented by formula (14) dissolved in tetrahydrofuran (8.4 mL) was added dropwise over one hour, and the mixture was allowed to react under reflux conditions for 0.5 hours. Subsequently, sodium carbonate (0.06 g) dissolved in water (0.4 mL) was added to the reaction mixture. To the resultant mixture, a solution of the 1st-generation dendrimer boronic acid derivative (0.7 g) represented by formula (14) dissolved in tetrahydrofuran (8.4 mL) was added dropwise over one hour, and the mixture was allowed to react under reflux conditions for four hours. After completion of reaction, the reaction mixture was cooled to room temperature, and water (20 mL) was added thereto. The resultant reaction mixture was subjected to extraction with chloroform, and the formed organic layer was washed with water. The organic layer was dried over sodium sulfate, and the solvent was distilled off under reduced pressure, to thereby yield a crude product. The crude product was subjected to isolation/purification through column chromatography (packing material: Silicagel 60 (product of Merck), eluent: methylene chloride/n-hexane) and then recrystallized from chloroform, to thereby yield 1.01 g of the target product, a 1st-generation, 3-branched dendrimer (pale yellow solid, yield: 56%). The yield was confirmed to be enhanced through continuous and intermittent addition of organic boron compound and intermittent addition of base catalyst. The structure of the obtained product was confirmed from the fact that the $^1$H-NMR spectrum coincides with that of the product through the aforementioned <Suzuki coupling not employing continuous/intermittent addition of organic boron compound nor intermittent addition of base catalyst> and the fact that molecular weight values (obtained through GPC) of the target product almost coincide those of the aforementioned product.

INDUSTRIAL APPLICABILITY

Since the production method of the present invention is based on the "convergent method," which does not require excessive amounts of starting materials and facilitates purification of synthesis intermediates, a high-purity dendrimer having no defects can be synthesized at high efficiency. Therefore, a novel dendrimer having a thienylene moiety, which is a promising useful polymer material for producing a variety of high-function materials in the fields of chemistry, pharmaceuticals, electronic materials, etc., can be provided.

The invention claimed is:

1. A method for producing a dendrimer having a structural repeating unit which is represented by formula (1) and which contains a linear portion including a thienylene moiety and a branch portion Y formed of an optionally substituted trivalent organic group, the method being based on the convergent method, characterized in that the method comprises reaction step 1 of converting α-position hydrogen of the thiophene ring of a thienylene-moiety-containing compound (a) for forming end moieties to an active group $V_1$ which undergoes Suzuki cross-coupling reaction, to thereby form compound (b); reaction step 2 of subjecting a compound (c) to Suzuki cross-coupling reaction with the compound (b) to thereby yield compound (d), the compound (c) having a linear portion and a branch portion Y and having, at the branch portion Y, two active groups $V_2$ which undergo Suzuki cross-coupling reaction with the active group $V_1$ reaction step 3 of converting α-position hydrogen of the thiophene ring of the thus-formed compound to an active group $V_1$ which undergoes Suzuki cross-coupling reaction, and reacting the compound (c) with the active group $V_2$, to thereby form a dendron of a subsequent generation; and a step of repeating the reaction step 3 in accordance with needs, to thereby form a dendrimer:

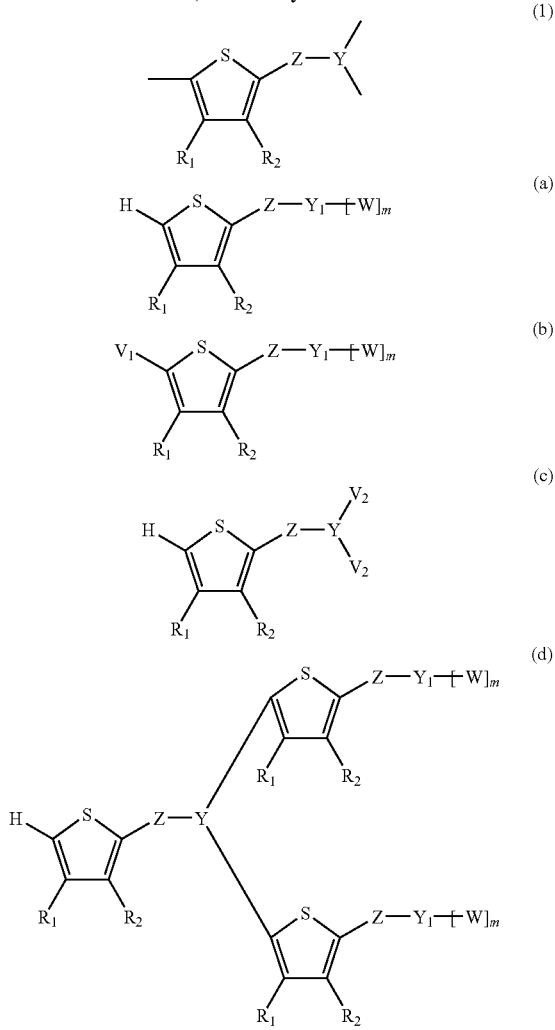

(wherein Z represents a single bond or an optionally substituted divalent organic group having no active group; each of $R_1$ and $R_2$ is selected from among a hydrogen atom, an alkyl group, and an alkoxy group; Y represents an optionally substituted trivalent organic group; $Y_1$ is identical to Y or represents an organic group having a skeleton identical to that of Y; W may be absent or represents an optionally substituted monovalent organic group having no active group; m is an integer of 0 or more; and each of $V_1$ and $V_2$ serving as active groups is selected from active groups which undergo Suzuki cross-coupling reaction, $V_1$ and $V_2$ being able to be mutually cross-coupled, and wherein $V_1$ is —B(OH)$_2$ and $V_2$ is —Br).

2. A method for producing a dendrimer according to claim 1, wherein, in the case where a compound used in the Suzuki cross-coupling reaction is a thiophene organic boron compound containing boron, the thiophene organic boron compound is gradually added in a continuous or intermittent manner to a reaction system containing the other counterpart compound, thereby performing Suzuki cross-coupling reaction.

3. A method for producing a dendrimer according to claim 1, which further includes a reaction step of converting α-position hydrogen of the thiophene ring of a compound (e) produced through singly or repeatedly carrying out the reaction step 3 to an active group $V_1$, to thereby form a compound (f); and a reaction step of reacting the compound (f) with a compound (g) having $Y_2$ serving as a core, to thereby form a compound represented by formula (2):

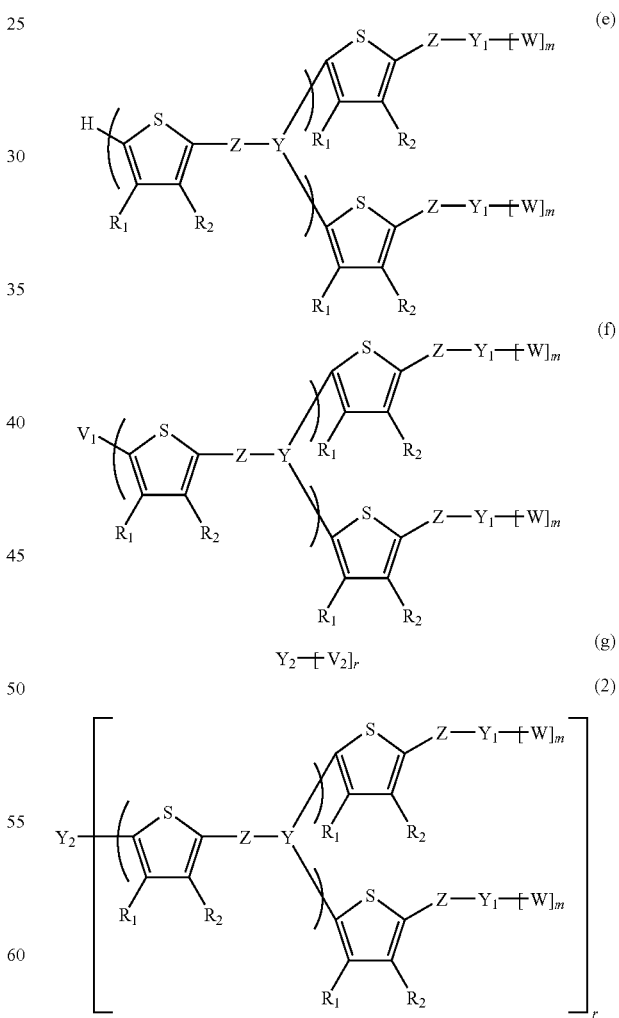

(wherein $Y_2$ represents an r-valent organic group, and r is an integer of 1 or more).

* * * * *